(12) United States Patent
Kravis et al.

(10) Patent No.: US 9,986,964 B2
(45) Date of Patent: Jun. 5, 2018

(54) INTRAORAL SENSOR POSITION DETECTION FOR FULL MOUTH IMAGE

(71) Applicant: Dental Imaging Technologies Corporation, Hatfield, PA (US)

(72) Inventors: Scott David Kravis, Lambertville, NJ (US); Jeremy Charnegie, Emmaus, PA (US); Adam T. Palermo, Philadelphia, PA (US)

(73) Assignee: DENTAL IMAGING TECHNOLOGIES CORPORATION, Hatfield, PA (US)

( * ) Notice: Subject to any disclaimer, the term of this patent is extended or adjusted under 35 U.S.C. 154(b) by 197 days.

(21) Appl. No.: 15/000,622

(22) Filed: Jan. 19, 2016

(65) Prior Publication Data

US 2016/0262716 A1 Sep. 15, 2016

Related U.S. Application Data

(63) Continuation-in-part of application No. 14/643,920, filed on Mar. 10, 2015, now Pat. No. 9,907,530.

(51) Int. Cl.
*A61B 6/14* (2006.01)
*A61B 6/00* (2006.01)
*A61B 6/08* (2006.01)

(52) U.S. Cl.
CPC ............... *A61B 6/547* (2013.01); *A61B 6/08* (2013.01); *A61B 6/145* (2013.01); *A61B 6/463* (2013.01); *A61B 6/5205* (2013.01); *A61B 6/587* (2013.01)

(58) Field of Classification Search
CPC .... G03B 42/042; G03B 42/04; G03B 42/047; G03B 42/025; A61B 6/145; A61B 6/14
(Continued)

(56) References Cited

U.S. PATENT DOCUMENTS 5,113,424 A 5/1992 Burdea et al.
7,090,395 B2 8/2006 Glazer
(Continued)

FOREIGN PATENT DOCUMENTS

WO 2012/127117 A1 9/2012

OTHER PUBLICATIONS

Extended European Search Report from the European Patent Office for Application No. 16158765.4 dated Mar. 15, 2017 (11 pages).
(Continued)

*Primary Examiner* — Don Wong
(74) *Attorney, Agent, or Firm* — Michael Best & Friedrich LLP

(57) ABSTRACT

Methods, systems, and devices for determining characteristics of an intraoral dental imaging sensor. A method includes providing an intraoral dental imaging sensor having a housing and a magnetic field sensor disposed in or on the housing, placing the intraoral dental imaging sensor in a holder, positioning the intraoral dental imaging sensor and at least part of the holder in a mouth of a patient, attaching a reference magnet to the patient, receiving, by an electronic processor, magnetic field data from the magnetic field sensor, determining, by the electronic processor, information including a position of the intraoral dental imaging sensor in the mouth of the patient based at least in part on the magnetic field data, and detecting x-rays by the intraoral dental imaging sensor to produce image data.

24 Claims, 35 Drawing Sheets

(58) Field of Classification Search
USPC .................................................. 378/181, 191
See application file for complete search history.

(56) References Cited

U.S. PATENT DOCUMENTS

| | | |
|---|---|---|
| 7,599,538 B2 | 10/2009 | Crucs |
| 7,775,713 B2 | 8/2010 | Klemola et al. |
| 2006/0257816 A1 | 11/2006 | Klemola et al. |
| 2006/0285637 A1 | 12/2006 | Varjonen et al. |
| 2012/0307965 A1* | 12/2012 | Bothorel .................. A61B 6/14 378/10 |
| 2013/0051528 A1* | 2/2013 | Inglese .................... A61B 6/08 378/62 |
| 2014/0010349 A1 | 1/2014 | De Godzinsky et al. |
| 2014/0161235 A1 | 1/2014 | Taskinen et al. |
| 2014/0086389 A1* | 3/2014 | Baek ...................... A61B 6/587 378/62 |
| 2014/0112439 A1* | 4/2014 | Berger ................. A61B 6/4494 378/62 |
| 2014/0191852 A1 | 7/2014 | Inglese et al. |

OTHER PUBLICATIONS

Partial European Search Report from the European Patent Office for Application No. 16158765.4 dated Jul. 20, 2016 (7 pages).

* cited by examiner

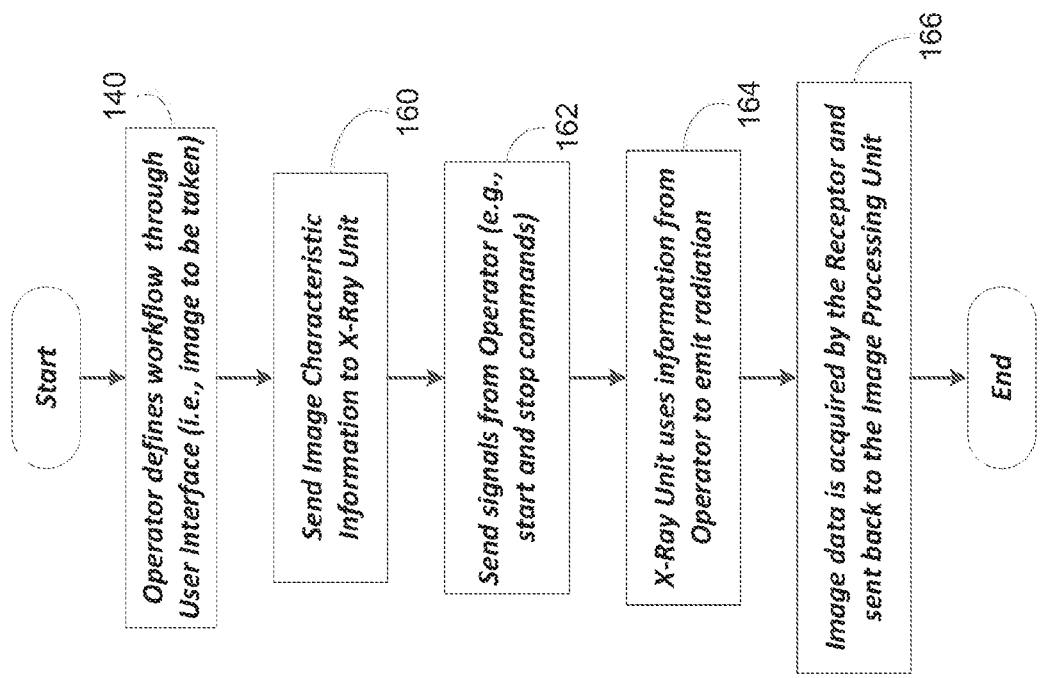

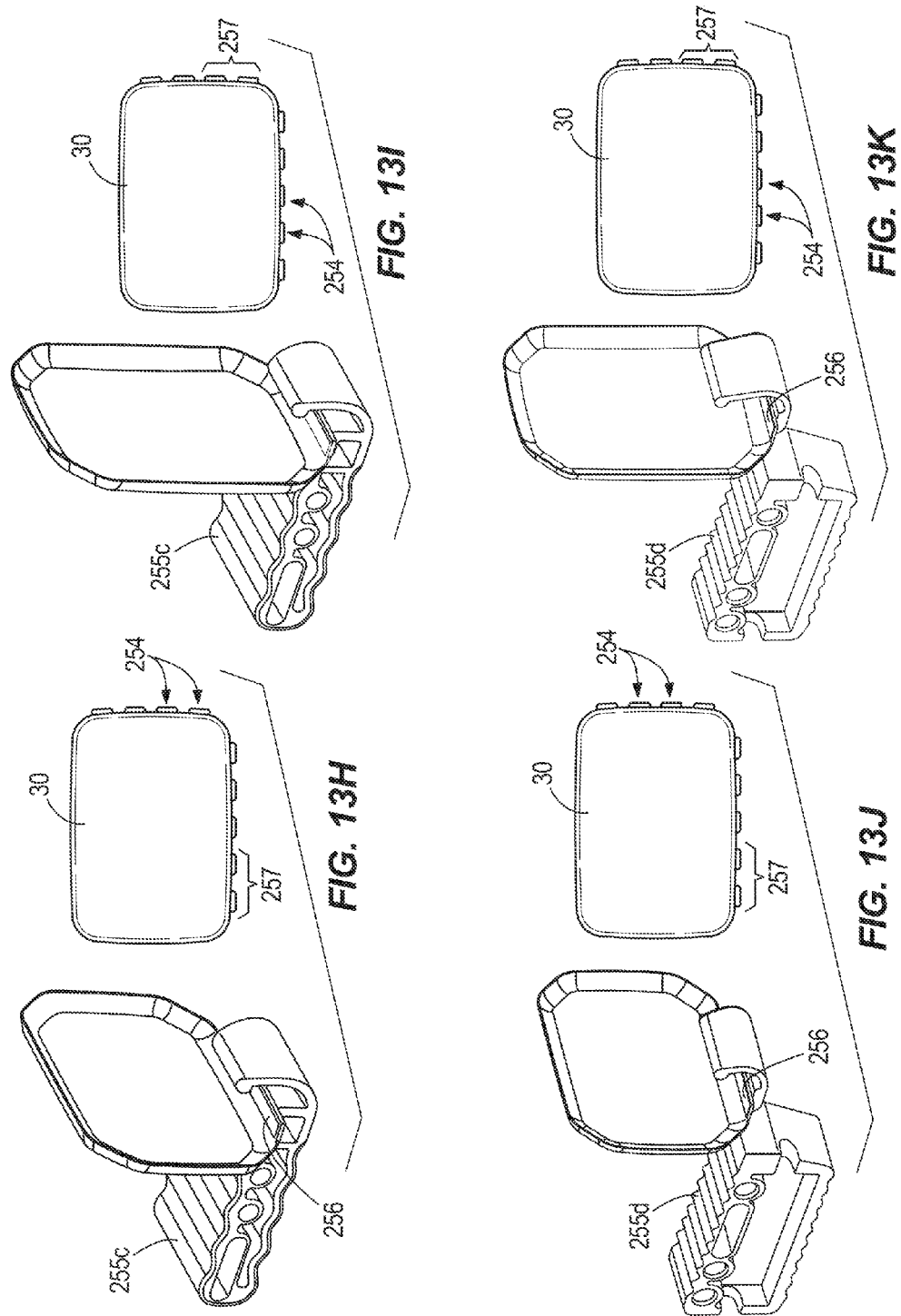

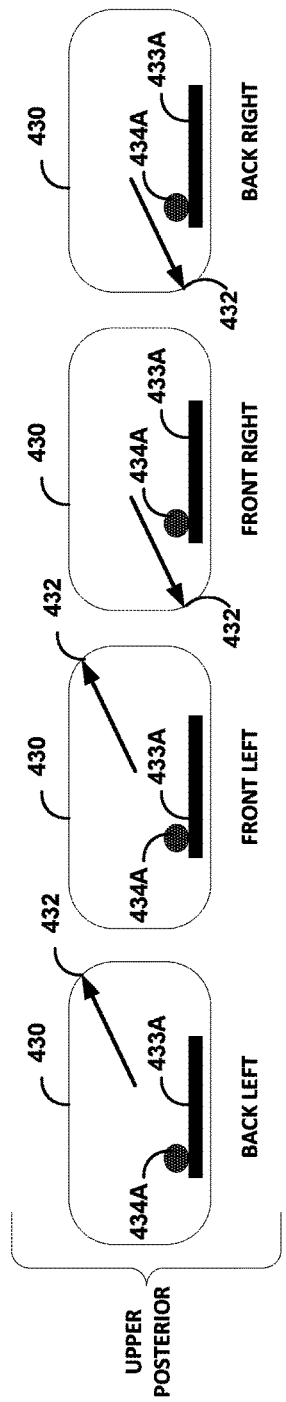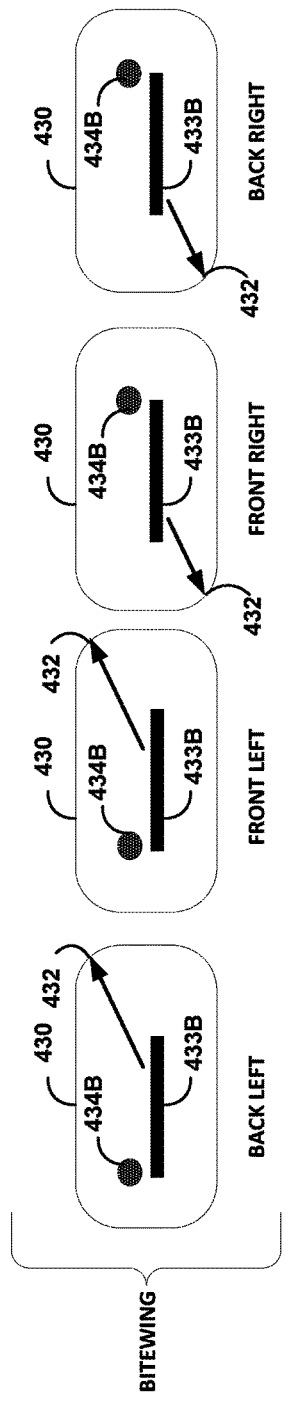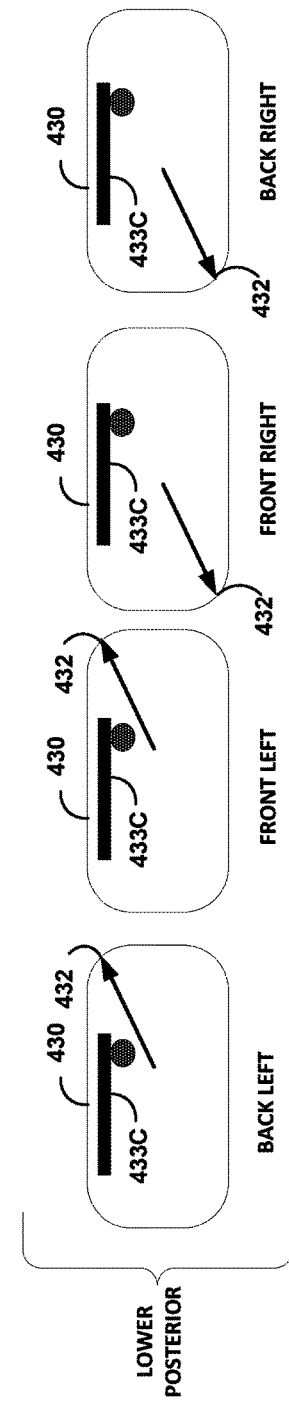

600B

626 — EXTERNAL MAGNETIC FIELD DATA

A-H

| UPPER POSTERIOR BACK LEFT 628A | UPPER POSTERIOR FRONT LEFT 628B | UPPER ANTERIOR LEFT 628N | UPPER ANTERIOR MIDDLE 628O | UPPER ANTERIOR RIGHT 628P | UPPER POSTERIOR FRONT RIGHT 628G | UPPER POSTERIOR BACK RIGHT 628H |
|---|---|---|---|---|---|---|
| BITEWING BACK LEFT 628C | BITEWING FRONT LEFT 628D | | | | BITEWING FRONT RIGHT 628J | BITEWING BACK RIGHT 628K |
| LOWER POSTERIOR BACK LEFT 628E | LOWER POSTERIOR FRONT LEFT 628F | LOWER ANTERIOR LEFT 628Q | LOWER ANTERIOR MIDDLE 628R | LOWER ANTERIOR RIGHT 628S | LOWER POSTERIOR FRONT RIGHT 628L | LOWER POSTERIOR BACK RIGHT 628M |

FULL MOUTH SERIES OF IMAGES 628

FIG. 38B

INTRAORAL SENSOR POSITION DETECTION FOR FULL MOUTH IMAGE

CROSS-REFERENCE TO RELATED APPLICATION

This application is a continuation-in-part of U.S. patent application Ser. No. 14/643,920, filed Mar. 10, 2015, the entire content of which is hereby incorporated by reference.

FIELD

The present invention relates to intra-oral x-ray systems. More particularly, the invention relates to systems and methods for automatically adjusting exposure parameters for an intra-oral x-ray system.

BACKGROUND

When acquiring intraoral x-ray images, exposure parameters (e.g., voltage, current, and exposure times) can be manually set by an x-ray technician or operator on a user interface that is used to control the x-ray source. Ideally, the exposure parameters should be adjusted based on, among other things, the particular teeth or the particular anatomy being imaged (e.g., anterior teeth, posterior teeth, bitewing (crowns of the posterior teeth), endodontic (tooth pulp), etc.). It is also generally desirable that the exposure parameters be adjusted to minimize x-ray exposure to the patient while still providing a quality image.

SUMMARY

Even though it is generally known that exposure parameters should be adjusted, in practice they are often not. In addition, the parameters are sometimes adjusted incorrectly.

Accordingly, one embodiment of the invention provides a system for automatically controlling or setting exposure parameters for an intra-oral dental x-ray system. Because the parameters ideally vary based on the particular teeth or anatomy being imaged, the system automatically identifies what teeth are being imaged based on at least one of two factors: 1) an assumed predetermined order of image acquisition; and 2) information from receptor holders used when taking the x-ray images.

The receptor holders include different types of holders and each type of holder is designed to hold a sensor or receptor in a position that is suited for a particular type of image acquisition. The holders are designed to provide to an x-ray exposure controller identification information correlated to the type of image being acquired. After receiving the identification information, the controller automatically adjusts the exposure parameters to match the teeth or anatomy associated with the particular holder. Thus, the system automatically adjusts the exposure parameters without requiring input from an x-ray technician or operator.

As is known, a full-mouth series of intra oral x-ray images includes a number of images. In most cases, full-mouth series includes eighteen (18) images or "films": four bitewings, eight posterial periapicals, and six anterior periapicals. The four bitewings typically include two molar bitewings (left and right) and two premolar bitewings (left and right). The eight posterior periapicals typically include two maxillary molar periapicals (left and right), two maxillary premolar periapicals (left and right), two mandibular molar periapicals (left and right), and two mandibular premolar periapicals (left and right). The six anterior periapicals typically include two maxillary canine-lateral incisor periapicals (left and right), two mandibular canine-lateral incisor periapicals (left and right), and two central incisor periapicals (maxillary and mandibular). Certain embodiments of the invention, can adjust the exposure parameters to accommodate differences in each of the images in a full mouth series.

In one embodiment, the invention provides a dental x-ray system comprising an intraoral dental imaging sensor, a holder, a reference magnet, and an image processing unit. The intraoral dental imaging sensor having a housing, an x-ray imaging sensor located in the housing and configured to capture x-ray energy and output x-ray image data, and a magnetic field sensor disposed in or on the housing and configured to sense one or more magnetic fields and output magnetic field data based on the one or more magnetic fields. The holder is configured to position the intraoral dental imaging sensor in a mouth of a patient. The reference magnet is configured to be disposed on the patient. The image processing unit is communicatively coupled to the intraoral dental imaging sensor and having memory and an electronic processor electrically coupled to the memory. The electronic processor is configured to receive the magnetic field data from the magnetic field sensor, and determine a position of the intraoral dental imaging sensor in the mouth of the patient based at least in part on the magnetic field data.

In another embodiment, the invention provides an intraoral dental imaging sensor comprising a housing, an x-ray imaging sensor, a magnetic field sensor, and an electronic processor. The x-ray imaging sensor is located in the housing and configured to receive x-rays and output image data. The magnetic field sensor is disposed in or on the housing and configured to sense one or more magnetic fields and output magnetic field data. The electronic processor is configured to receive the magnetic field data and determine a position of the intraoral dental imaging sensor in a mouth of a patient based at least in part on the magnetic field data.

In yet another embodiment the invention provides a method for intraoral dental imaging. The method includes providing an intraoral dental imaging sensor having a housing and a magnetic field sensor disposed in or on the housing, placing the intraoral dental imaging sensor in a holder, positioning the intraoral dental imaging sensor and at least part of the holder in a mouth of a patient, attaching a reference magnet to the patient, receiving, by an electronic processor, magnetic field data from the magnetic field sensor, determining, by the electronic processor, a position of the intraoral dental imaging sensor in the mouth of the patient based at least in part on the magnetic field data, and detecting x-rays by the intraoral dental imaging sensor to produce image data.

In another embodiment, the invention provides a non-transitory computer-readable medium comprising instructions that when executed by an electronic processor perform a set of functions comprising receiving magnetic field data from a magnetic field sensor disposed in or on a housing of an intraoral dental imaging sensor, and determining a position of the intraoral dental imaging sensor in a mouth of a patient based at least in part on the magnetic field data.

In yet another embodiment, the invention provides a holder for an intraoral dental imaging sensor comprising a housing configured to position and support the intraoral dental imaging sensor in a mouth of a patient, and a magnet attached to the housing, wherein a characteristic of the magnet is configured to indicate a type of the holder.

Other aspects of the invention will become apparent by consideration of the detailed description and accompanying drawings.

BRIEF DESCRIPTION OF THE DRAWINGS

FIG. 5B is a flow chart illustrating an alternative method of automatically adjusting exposure parameters using an x-ray source controller included in the x-ray system of FIG. 1A or 2.

FIGS. 13D-K illustrate various types of receptor holders used in the x-ray system of FIG. 1A or 2 in different orientations and the corresponding engaging contacts of the receptor of FIG. 13A.

FIGS. 20-23 are schematic views of an intraoral dental imaging sensor and a bite block of an upper posterior holder with a magnet.

FIGS. 24-27 are schematic views of an intraoral dental imaging sensor and a bite block of a bitewing holder with a magnet.

FIGS. 28-31 are schematic views of an intraoral dental imaging sensor and a bite block of a lower posterior holder with a magnet.

FIGS. 38A and 38B are flowcharts of a method for capturing and organizing a full mouth series of images in a particular sequence from the intraoral dental imaging sensor of FIGS. 20-37 using the dental x-ray system of FIG. 18.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1A:
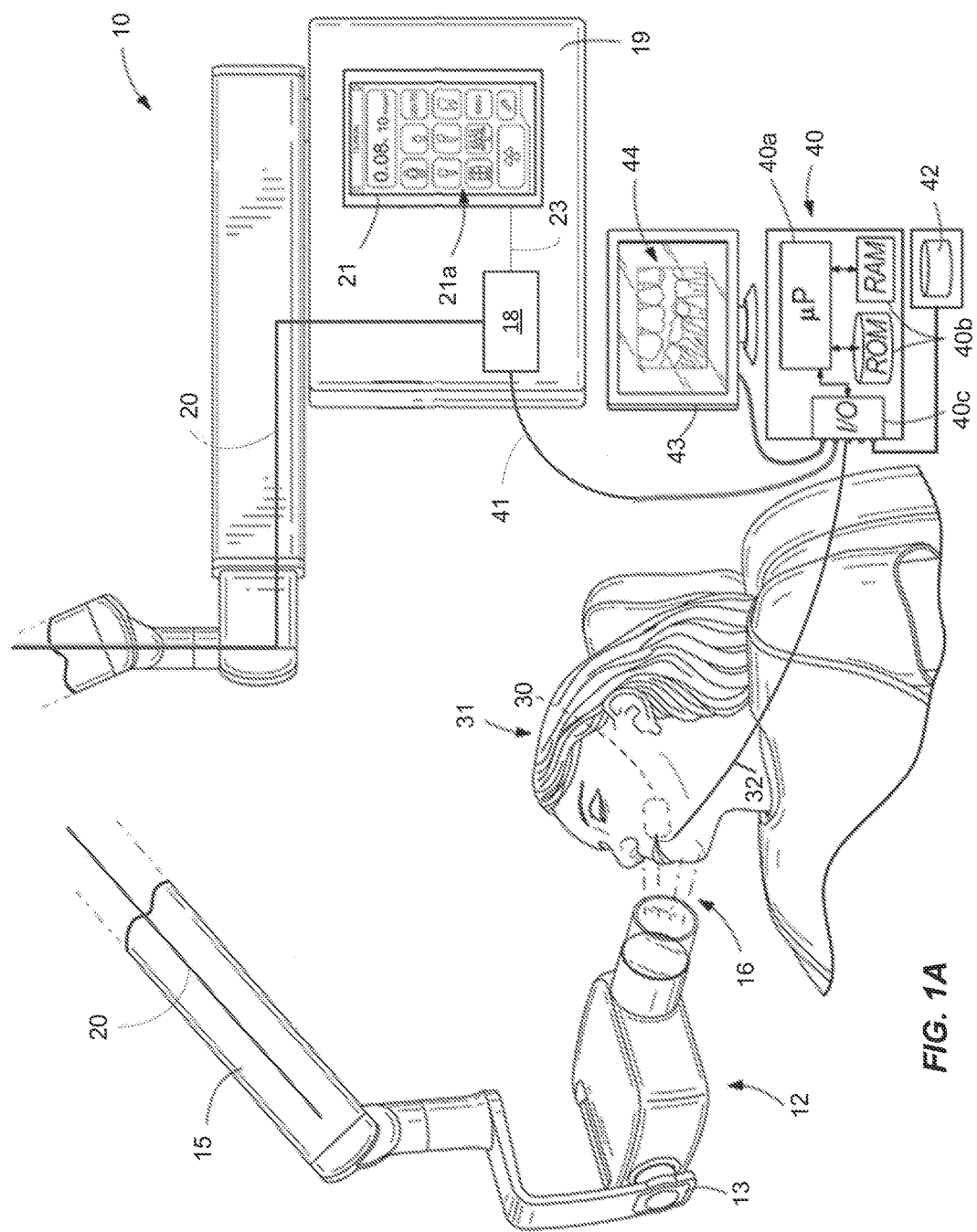
FIGS. 1A and 2 schematically illustrate an intra-oral dental x-ray system.

FIG. 1A illustrates an intraoral dental x-ray system 10. The system 10 includes an x-ray source 12. In the illustrated embodiment, the source 12 is located at an end 13 of a mechanical arm 15. When activated, the x-ray source 12 generates an x-ray stream 16 that has a generally circular cross-section. (Although x-rays are generally invisible, a representation of a stream is illustrated to facilitate understanding of the invention.) In some applications, a collimator (not shown) is used to reduce the size of the stream 16 and generate a smaller x-ray stream having a different shaped cross-section (e.g., rectangular). The collimator can also be used to change the shape of the beam and/or focus the stream on a particular anatomical site of interest. As described below in more detail, the x-ray source 12 includes at least one adjustable exposure parameter.

The system 10 also includes a controller 18. As illustrated in FIG. 1A, the controller 18 can be included inside a housing 19 located at the base or shoulder of the arm 15. In this configuration, the controller 18 is connected to the x-ray source 12 using a connection 20 (e.g., a wire, cable, wireless connection, or the like) that runs from the x-ray source 12 to the controller 18 through the arm 15. It should be understood that although the controller 18 is illustrated as being inside the housing 19 at the base of the mechanical arm 15, in some embodiments the controller 18 is located within the housing of the x-ray source 12.

Figure 1B:
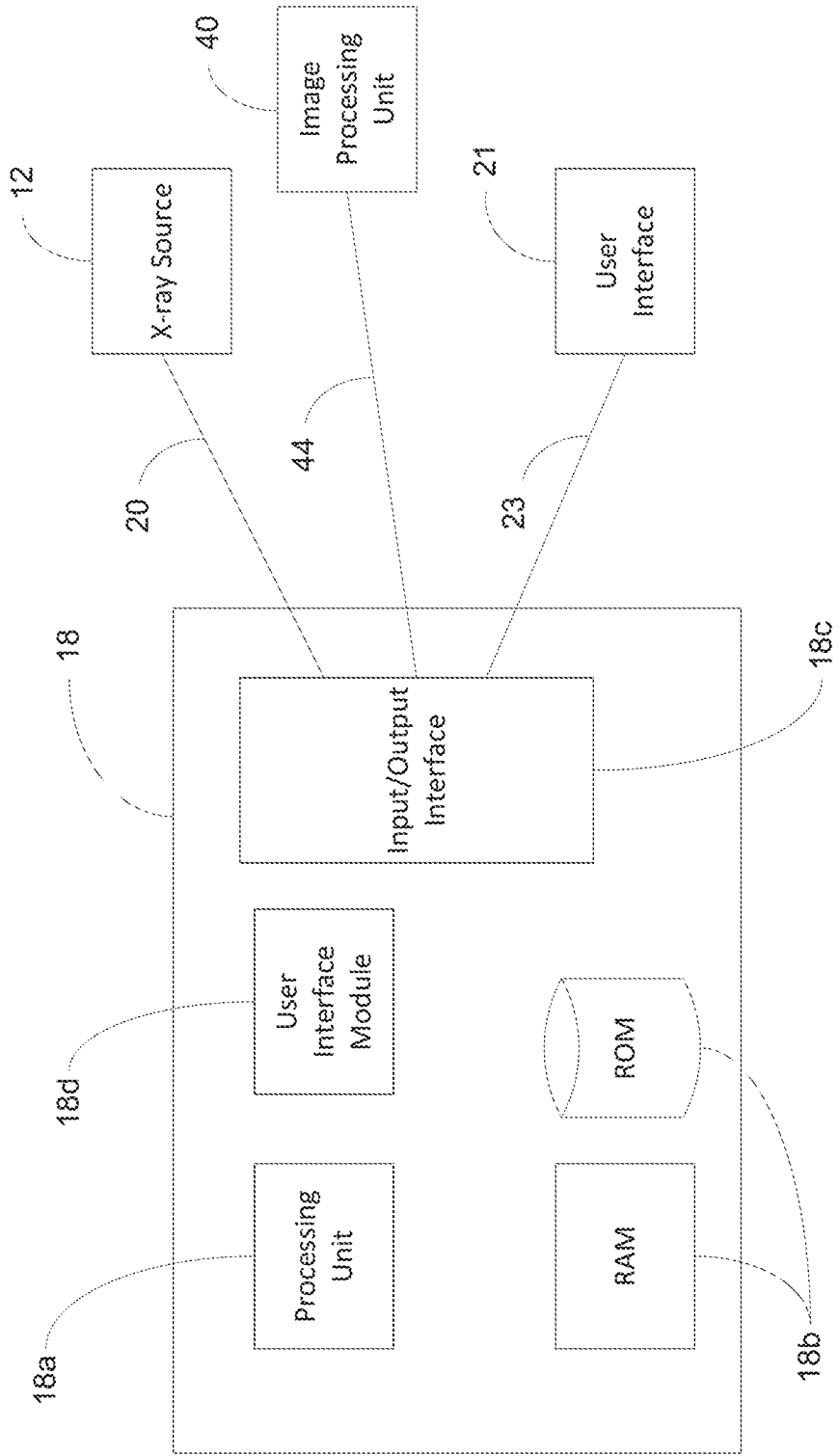
FIG. 1B schematically illustrates a controller included in the x-ray system of FIG. 1A

The controller 18 and the x-ray source 12 are collectively referred to as an x-ray unit. The controller 18 monitors and controls operation of the x-ray source 12. As illustrated in FIG. 1B, the controller 18 includes a processing unit 18a, which can be, for example, a microprocessor or an application-specific integrated circuit ("ASIC"). The controller 18 also includes one or more non-transitory memory modules 18b, for example, a random access memory ("RAM") module and a read-only memory ("ROM") module. The memory modules 18b can store software and/or associated data for monitoring and controlling the x-ray source 12 and/or other aspects of the system 10.

In addition, the controller 18 includes an input/output interface 18c. The input/output interface 18c communicates with systems and devices external to the controller 18, including the x-ray source 12 and a user interface 21. In some embodiments, the controller 18 also includes a user interface module 18d. The user interface module 18d can be configured to communicate with the user interface 21 (e.g., over a universal serial bus ("USB") cable). For example, the user interface module 18d can be configured to generate screens for display on the user interface 21. In addition, the user interface module 18d can be configured to receive inputs from an operator received through the user interface 21. Accordingly, in some embodiments, the user interface module 18d communicates with the user interface 21 rather than the input/output interface 18c.

Figure 2:
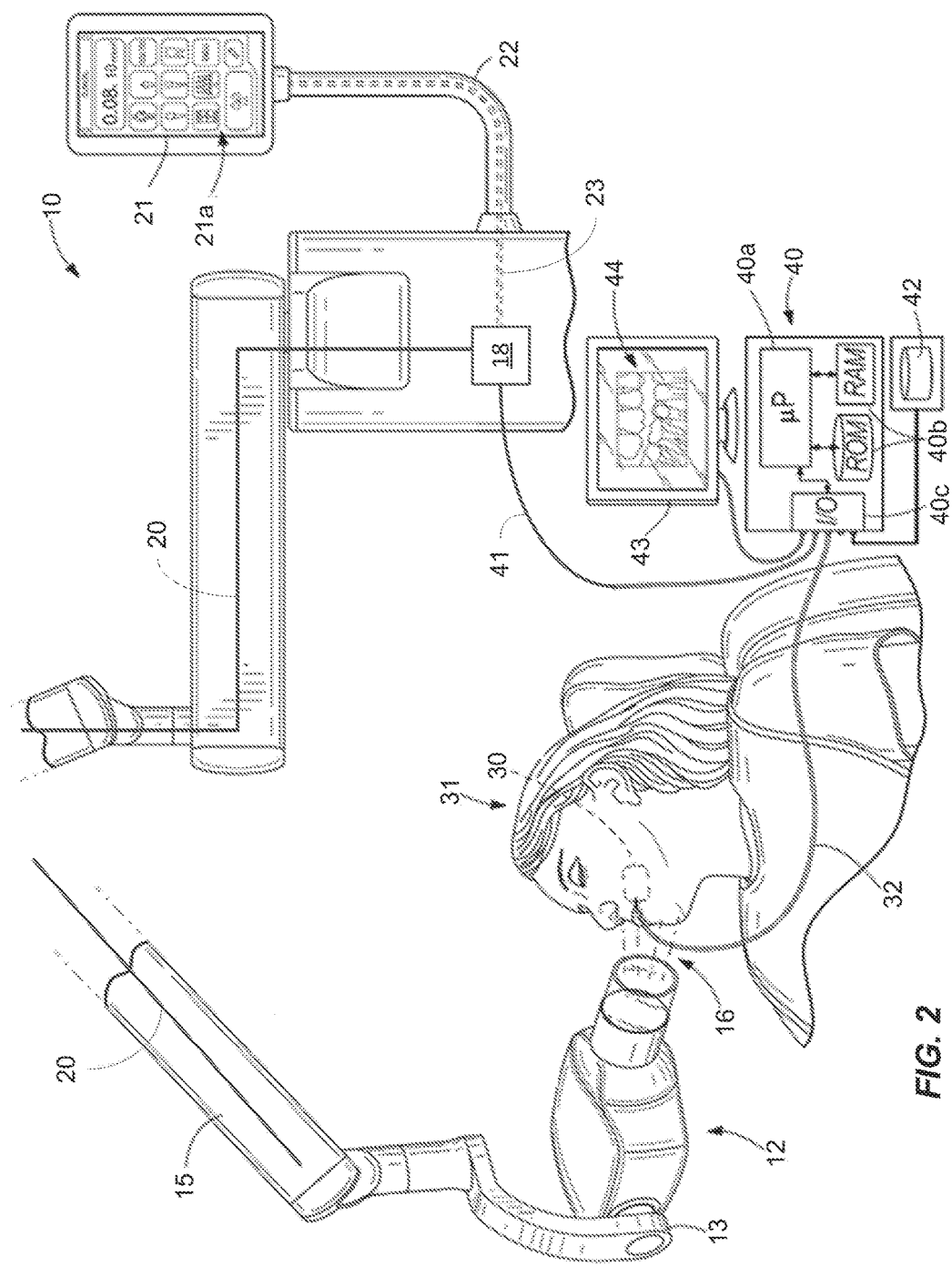

As illustrated in FIGS. 1A and 2, in some embodiments, the user interface 21 includes a touchscreen 21a. However, it should be understood that the user interface 21 can include different types of input and output devices and combinations of the same (e.g., a keyboard, tactile buttons, a joystick, a mouse, a non-touch screen display, etc.). The user interface 21 is located external to x-ray source 12 and the controller 18. In some embodiments, the user interface 21 is contained within the housing 19 located at the base or shoulder of the arm 15 (see FIG. 1A). In other embodiments, the user interface 21 can be mounted on a separate extension 22 connected to the arm 15 (see FIG. 2). In some embodiments, the extension 22 is flexible to allow an operator to change the position of the user interface 21. It should be understood that the user interface 21 can also be located outside of the room where the x-ray source is located to allow the operator to avoid radiation exposure. In other embodiments, the user interface 21 can be located in the same room as the x-ray source but protected from radiation exposure using shielding material.

Regardless of where the user interface 21 is positioned, the user interface 21 is connected to the controller 18 (i.e., through the input/output interface 18c) over a connection 23. In some embodiments, the connection 23 (e.g., a wire or cable) between the controller 18 and the user interface 21 can be positioned external to the arm 15. However, in other embodiments, the connection 23 can be accomplished by routing a wire from the controller 18 to the user interface 21 internal to the housing 19. Also, in some embodiments, the user interface 21 can communicate with the controller 18 using a wireless connection, a wired connection, or a combination of wired and wireless connections. An operator can use the user interface 21 to manually control the x-ray source 12. In particular, an operator can use the user interface 21 to manually set one or more adjustable exposure parameters of the x-ray source 12. The exposure parameters can include a voltage (e.g., in kilovolts ("kV")), a current (e.g., in milliamps ("mA")), and an exposure time (e.g., in milliseconds ("ms")). The controller 18 receives the parameters and uses the parameters (in combination with the software and data stored in the memory modules 18b) to monitor and control the x-ray source 12.

In some embodiments, the x-ray source 12 is activated in response to a signal received from a remote switch (not shown). The remote switch communicates with the controller 18, which, in turn, starts and/or stops the x-ray stream 16. The remote switch can communicate with the controller 18 over a wired or wireless connection (e.g., through the input/output interface 18c). An operator can start and stop the x-ray source 12 using the remote switch from a different room or location than the x-ray source 12 to avoid radiation exposure.

As shown in FIGS. 1A and 2, the x-ray source 12 is positioned (e.g., manually by an operator (not shown)) so that the x-ray stream 16 is directed toward an intra-oral x-ray sensor or receptor 30 located in the mouth of a patient 31. The receptor 30 can include a digital detector, a sensor, a film plate, or an imaging plate (e.g., phosphorescent plate or other type of imaging plate). As described in more detail below, the receptor 30 is positioned within a holder prior to being inserted in the patient's mouth. The holder helps properly position the receptor 30 for imaging particular teeth or anatomy. Different holders are used depending on what teeth or region of the patient's mouth are being imaged. In the examples illustrated in FIGS. 1A and 2, a wire, cable, or similar connection 32 connects the receptor 30 to an image processing unit 40. The connection 32 between the receptor 30 and the image processing unit 40 can alternatively be a wireless connection, a fiber-optic connection, or other connection suitable for transmitting data between the devices. In some embodiments, the connection 32 also provides an electrical return path that allows electrical signals to be provided to and/or received from the receptor 30 and or a holder for the receptor 30. The electrical signals can be used to identify a type or placement of the receptor 30 that indicates what image in a sequence of images is being acquired. In other embodiments, a separate connection (e.g., a separate wire) is used to provide the electrical signals.

The image processing unit 40 includes a processing unit 40a, which can be, for example, a microprocessor or an ASIC. The image processing unit 40 also includes one or more non-transitory memory modules 40b, e.g., a RAM module and a ROM module. The memory modules 40b can store software and data for processing image data collected by the receptor 30 (e.g., to generate an image). The memory modules 40b can also store image data and/or associated metadata for the image data (e.g., a log of exposure times, etc.). In addition, as described in more detail below, the memory modules 40b can store software and data for automatically controlling exposure parameters. In some embodiments, the software stored on the memory modules 40b is the Dexis Imaging Suite provided by Dental Imaging Technology Corp.

As illustrated in FIGS. 1A and 2, the image processing unit 40 also includes an input/output interface 40c. The input/output interface 40c communicates with systems and devices external to the image processing unit 40, including, for example, the receptor 30 and the controller 18. For example, the image processing unit 40 can communicate with the controller 18 over a connection 41. The connection 41 can include a wire or a cable. In other embodiments, the connection 41 can include a wireless connection. Although the connection 41 illustrated in FIGS. 1A and 2 is shown as being external to the housing 19, it should be understood that the connection 41 can be routed through one or more components of the system 10 (e.g., the housing 19, the arm 15, etc.).

In some embodiments, the input/output interface 40c also communicates with one or more an external data storage devices 42 that store images acquired using the system 10. As also illustrated in FIGS. 1 and 2, the input/output interface 40c can also communicate with one or more display devices 43. The display device(s) 43 can be used to display images acquired through use of the system 10. In particular, during operation of the system 10, image data is captured by the receptor 30, the data is processed by the image processing unit 40, and the processed data is sent to a display device 43 where it can be viewed as an image 44. (Image 44 is drawn more distinctly than an x-ray image would typically appear.) In some embodiments, the display device(s) 43 include a touchscreen that receives input from an operator. The image processing unit 40 can also include one or more additional peripheral devices for receiving input from an operator (e.g., a keyboard, mouse, joystick, etc.).

It should be understood that the receptor 30 could be configured to carry out all or a portion of the image processing carried out by the image processing unit 40. In other words, imaging processing could be distributed between the receptor 30 and the unit 40. For example, processing hardware could be located in the body of the receptor 30 or in the connection 32 connecting the receptor 30 to the image processing unit 40.

As noted above, an operator can use the user interface 21 to set one or more adjustable exposure parameters for the x-ray source 12. To minimize radiation exposure to the patient and improve image quality, the exposure parameters should be varied based on the particular teeth being imaged. However, in many cases, operators do not adjust the parameters for different teeth images. Rather, operators typically set the exposure parameters once and use the same parameters for all images acquired for the patient. In addition, even if an operator adjusts the parameters for the particular image being acquired, the operator may incorrectly adjust the parameters or may not adjust the parameters to optimal values. Accordingly, it would be advantageous for the system 10 to be configured to automatically adjust the exposure parameters for the particular type of image being acquired.

Figure 3:
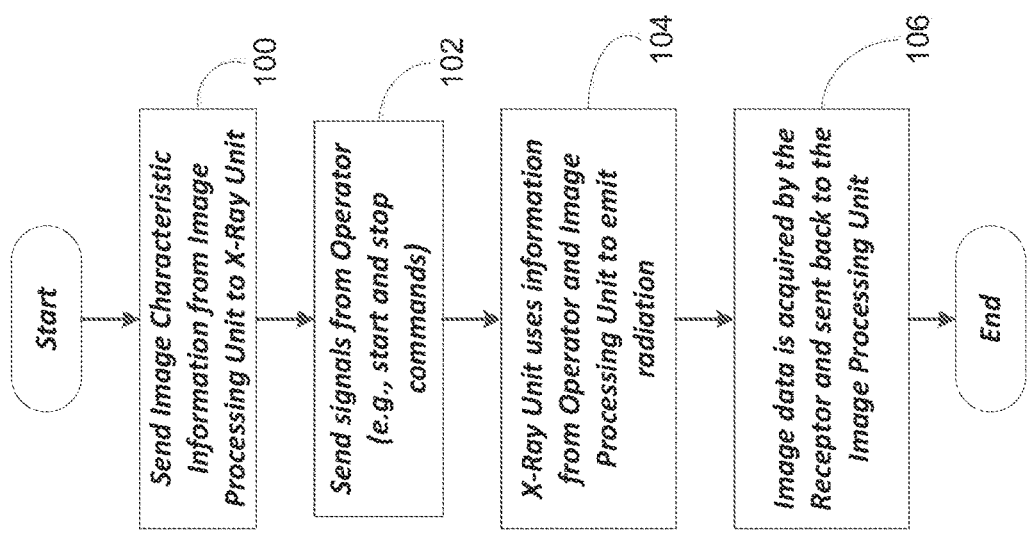
FIG. 3 is a flow chart illustrating a method of automatically adjusting exposure parameters using an image processing unit included in the x-ray system of FIG. 1A or 2.

For example, FIG. 3 is a flow chart illustrating one method for automatically adjusting the exposure parameters. As illustrated in FIGS. 1A, 1B, and 2, the image processing unit 40 communicates with the x-ray unit (e.g., the controller 18, which communicates with the x-ray source 12). Accordingly, the image processing unit 40 can send image characteristic information to the x-ray unit (at 100). As described in more detail below, the image characteristic information can include one or more values for adjustable exposure parameters (e.g., voltage, current, and exposure time), image type information (e.g., an image type identifier), or image sequence information (e.g., a sequence or series identifier). The controller 18 uses the image characteristic information to automatically adjust the exposure parameters for a particular image. As illustrated in FIG. 3, the operator can also provide commands or data to the x-ray unit (at 102). For example, the operator can provide commands to the x-ray unit through the user interface 21. The operator can also issue start and/or stop commands to the x-ray unit through a remote switch as described above.

The controller 18 operates the x-ray source 12 (at 104) according to the image characteristic information and any additional commands or data received from the operator. The receptor 30 captures image data based on the x-ray stream 16 generated by the x-ray source 12, and the image data is transmitted to the image processing unit 40 for processing and display (at 106).

Figure 4:
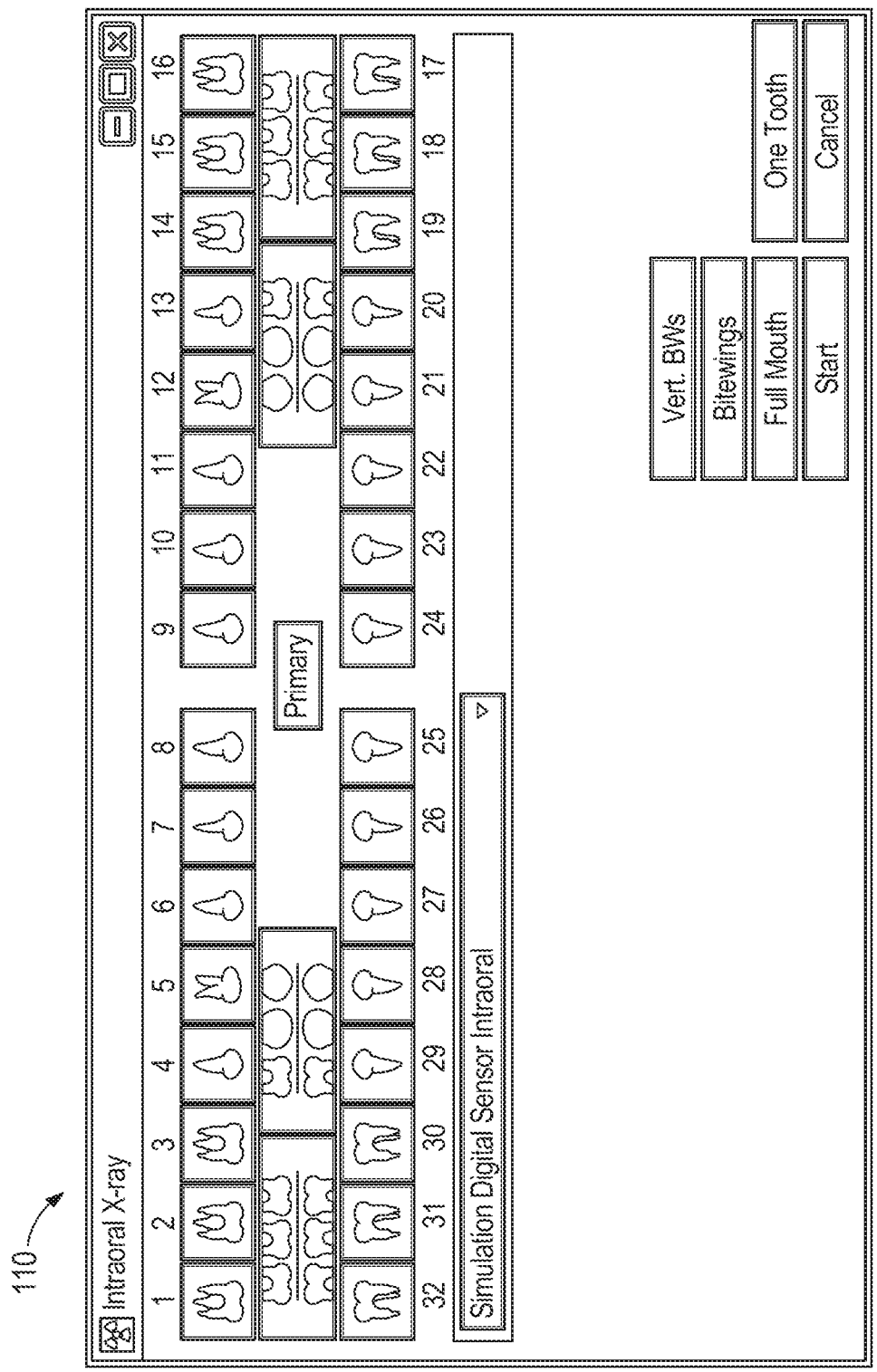
FIG. 4 is a screen illustrating a sequence of images included in a full mouth series.
Figure 5A:
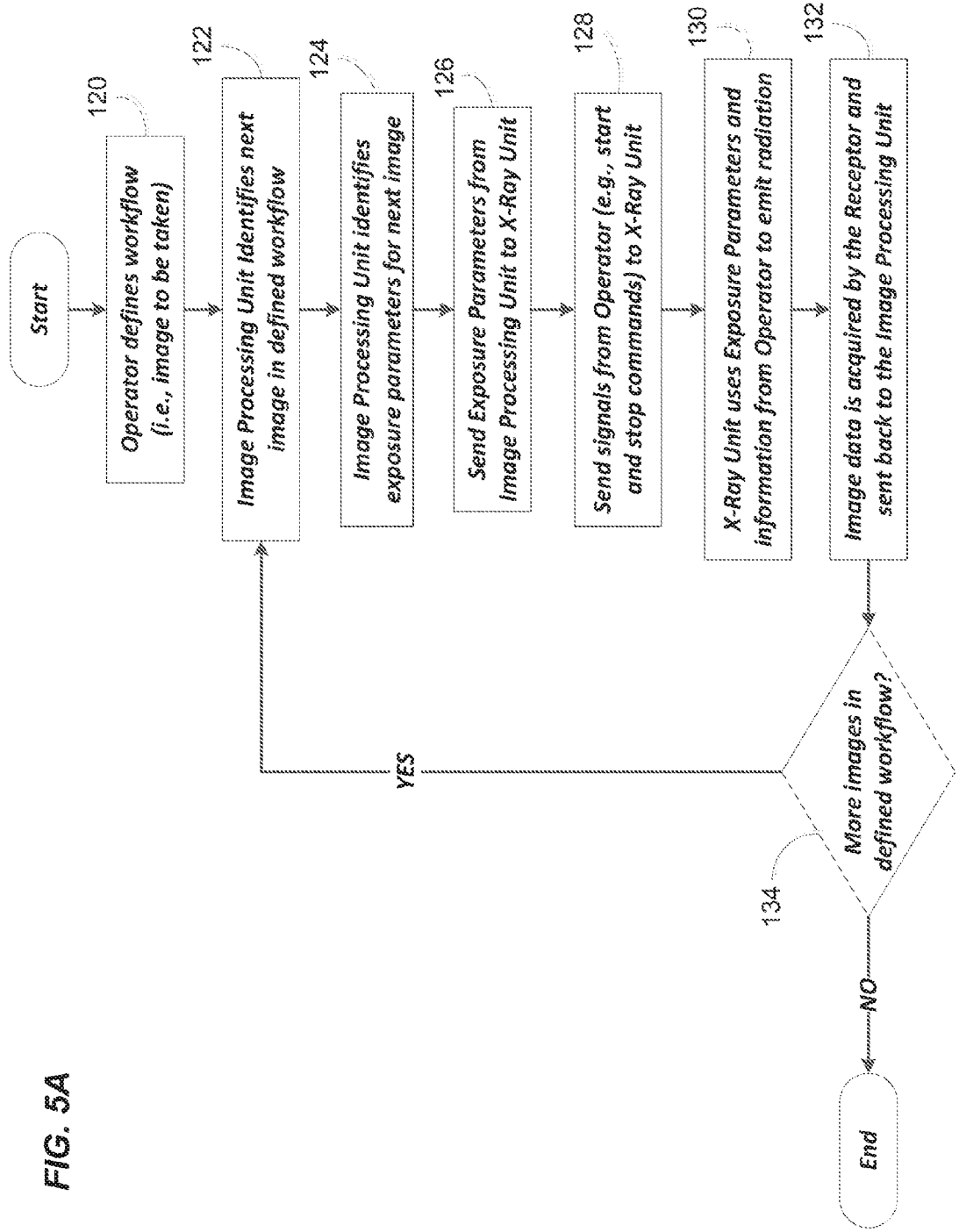
FIG. 5A is a flow chart illustrating a method of automatically adjusting exposure parameters for a sequence of images using an image processing unit included in the x-ray system of FIG. 1A or 2.

As noted above, the image characteristic information can include exposure parameters, an image sequence or series identifier, or an image type identifier. For example, in some embodiments, the image processing unit 40 is configured to perform particular series or sequences of image acquisitions. When the system 10 is used to perform a full mouth series, image data is captured by the receptor 30 according to a predefined sequence. For example, FIG. 4 illustrates a screen shot displayed by the image processing unit 40 illustrating a sequence of images obtained as part of a full mouth series (sometimes referred to as a "tooth map"). In some embodiments, as the images are acquired for a full mouth series, the tooth map 110 is updated to highlight the next image to be acquired. As noted, it is common for eighteen images to be obtained for a full mouth series, but more or fewer images may be obtained depending on the particular imaging sequence that is desired Accordingly, the image processing unit 40 can use a predefined sequence of image to identify the next image acquired by the system 10 and, consequently, the exposure parameters for such an image, which the unit 40 transmits to the controller 18 as the image characteristic information. For example, FIG. 5A illustrates a method for setting exposure parameters for a sequence of images. As illustrated in FIG. 5A, after a user defines the workflow (i.e., the image(s) to be taken in a predefined sequence) through the image processing unit 40 (at 120), the image processing unit 40 identifies the next image (i.e., the first image) in the predefined sequence associated with the defined workflow (at 122). The image processing unit 40 then identifies the exposure parameters for the next image (at 124). To identify exposure parameters associated with a particular image in a predefined sequence of image acquisitions, the image processing unit 40 (or an external data storage device 42) can store one or more data or look-up tables that map exposure parameters to particular image acquisitions. For example, without limitation, the memory modules 40b or an external data storage device 42 accessible by the image processing unit 40 can store a plurality of image types and a plurality of predetermined settings of at least one adjustable exposure parameter associated with the x-ray source 12. The image processing unit 40 can also associate each of the plurality of image types with one of the plurality of predetermined settings to form a data table. One sample data table is provided below. However, it should be understood that different data tables can be used for different types of patients (e.g., child versus adult), different types of imaging equipment or media (e.g., different receptors, different film speeds, etc.), different portions of anatomy being imaged, etc. For example, without limitation, typical voltage settings can range from about 60 kV to about 70 kV, typical current settings can range from about 4 mA to about 7 mA, and typical exposure times can range from about 0.2 seconds to about 1.0 seconds, but other values can also be used in accordance with embodiments of the present invention. In addition, in some cases (as illustrated in Table 1 below, for example) the voltage and current will be same for different types of images, whereas in other cases the voltage and current values may vary. Also, in some embodiments, the same exposure parameters can be associated with a sub-set of the images acquired as part of a full mouth scan. In particular, each image acquired as part of a full mouth series may not be associated with different exposure parameters.

TABLE 1

| Image Identifier | Voltage (kV) | Current (mA) | Exposure Time (ms) |
|---|---|---|---|
| Bitewing | 65 | 6 | 0.400 |
| Molar | 65 | 6 | 0.400 |
| Incisor | 65 | 6 | 0.250 |
| Bicuspid | 65 | 6 | 0.320 |
| Occlusal | 65 | 6 | 0.630 |

Accordingly, upon receiving the image characteristic information, the image processing unit 40 selects an image type (e.g., an image identifier) and accesses a data table associated with the selected image type. The image processing unit 40 uses the accessed data table to select one or more predetermined settings (i.e., values for one or more adjustable exposure parameters for the x-ray source 12). As described below, the image processing unit 40 transmits the predetermined settings to the controller 18, which uses the settings to automatically adjust one or more exposure parameters of the x-ray source. As mentioned above, in some embodiments, for a series or sequence of images, different sub-sets of the sequence of images can be associated with different settings. For example, the image processing unit 40 can be configured to use a data table to select a first set of values for the exposure parameters for a first sub-set of images included in a sequence of images and a second set of values for the exposure parameters for a second sub-set of images included in the sequence of images.

The image processing unit 40 can also be configured to measure the exposure level (signal level) of one or more previously-taken or acquired images to adjust the stored exposure parameters. For example, the image processing unit can compare a measured exposure level of a previous image to a preset optimum value (or an optimum range or window). If the observed exposure level is higher than optimum, this can indicate that the patient has received an unnecessarily high dose of x-rays, and if the observed exposure level is too low, the image quality may be sub-optimal. Once the difference from the optimum exposure value (or range) is determined, the image processing unit 40 corrects the lookup table exposure factors for the next image in the sequence with a level shift based on the difference. This adjustment can, for example, have the effect of automatically accounting for differences in patient size based on acquired images.

After the unit 40 identifies the exposure parameters associated with the next image (i.e., the first image) (at 124), the unit 40 transmits the identified exposure parameters to the controller 18 prior to the acquisition of the next image (at 126). The controller 18 uses the received exposure parameters and any information received from the operator (e.g., through the user interface 21) (at 128) to control the x-ray source 12 to emit radiation (at 130). Image data for the image is then acquired by the receptor 30 and sent back to the image processing unit 40 (at 132).

After receiving the image data for the first image, the image processing unit 40 determines if the user-defined workflow includes additional images (at 134). As noted above, a user-defined workflow can be associated with a predetermined order accessible by the image processing unit 40. Accordingly, the image processing unit 40 can determine whether additional images need to be taken by considering the predetermined order. Alternatively, if an operator prefers a different order than the predefined order for a particular series, the operator can designate the next image prior to each x-ray exposure (e.g., using a tooth map 110 as illustrated in FIG. 4, which can be displayed on a display device 43).

If the workflow includes additional images, the image processing unit 40 identifies the next image in the predefined sequence (e.g., based on the predetermined order or an operator designation) (at 122) and repeats the exposure parameter determination process as described above and sends the exposure parameter settings to the controller 18 prior to the next image acquisition. Alternatively, if the image processing unit 40 determines that the workflow does not include any additional images (i.e., the final image of the sequence has been acquired), the exposure parameter setting process ends.

In some embodiments, in addition to or as an alternative to including the exposure parameters, the image characteristic information includes an identifier of a particular image or a particular sequence of images. For example, as described above, an operator can select a particular predefined sequence of images or can select a custom sequence of images (e.g., by selecting individual images for acquisition). Accordingly, the image processing unit 40 can send an image identifier or an image sequence identifier to the controller 18, and the controller 18 can use the identifier to determine the exposure parameters for the next image acquisition, e.g., by using data table(s) as described above. For example, in some embodiments, the controller 18 stores the data table(s) described above (e.g., in one of the memory modules 18b) and uses the data tables directly to determine exposure parameters. Accordingly, it should be understood that the functionality of the image processing unit 40 can be distributed between the controller 18 and the unit 40 in various combinations.

Figure 5C:
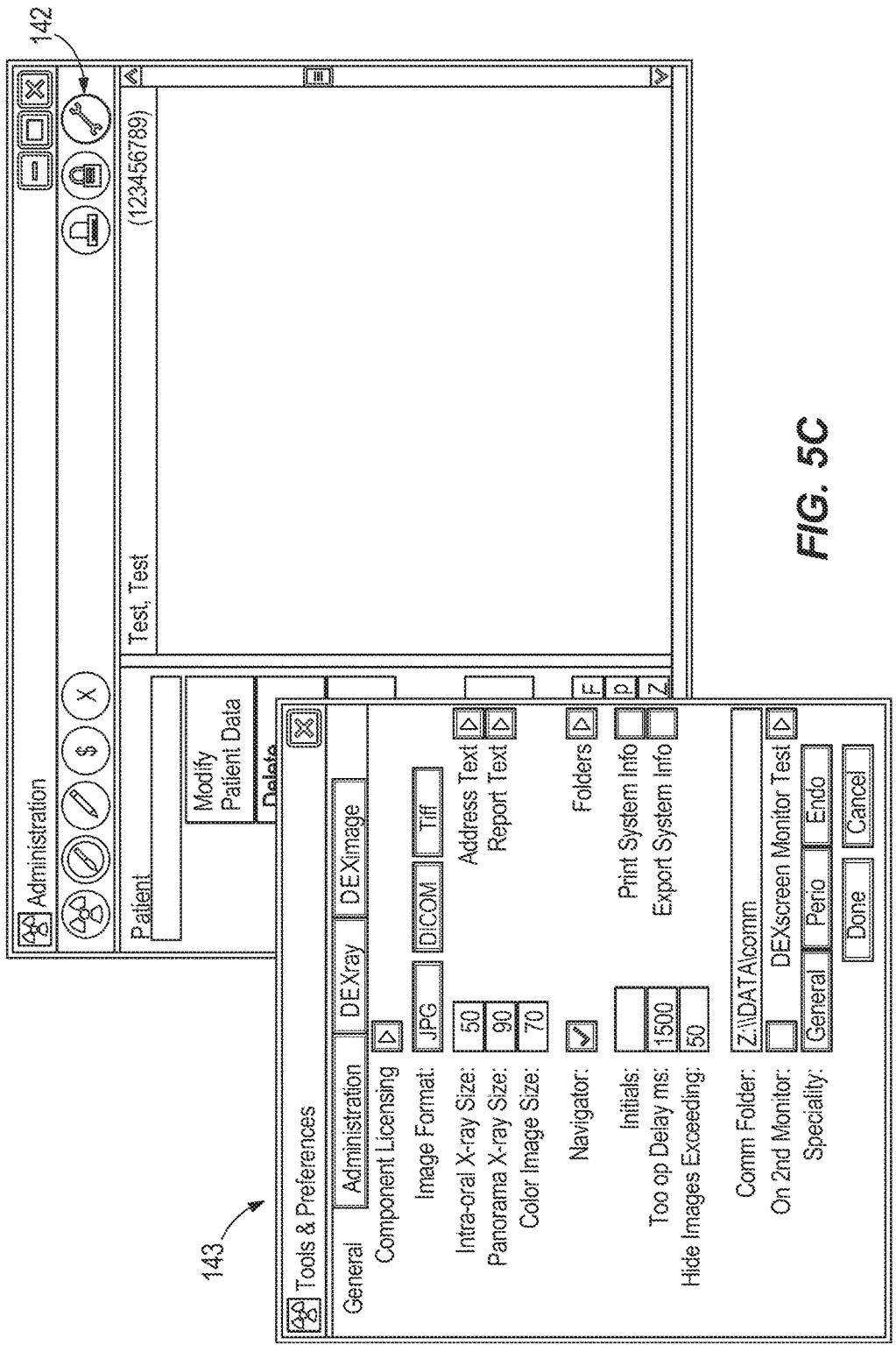
FIGS. 5C-F illustrate a user interface for creating a customized scan sequence.
Figure 5D:
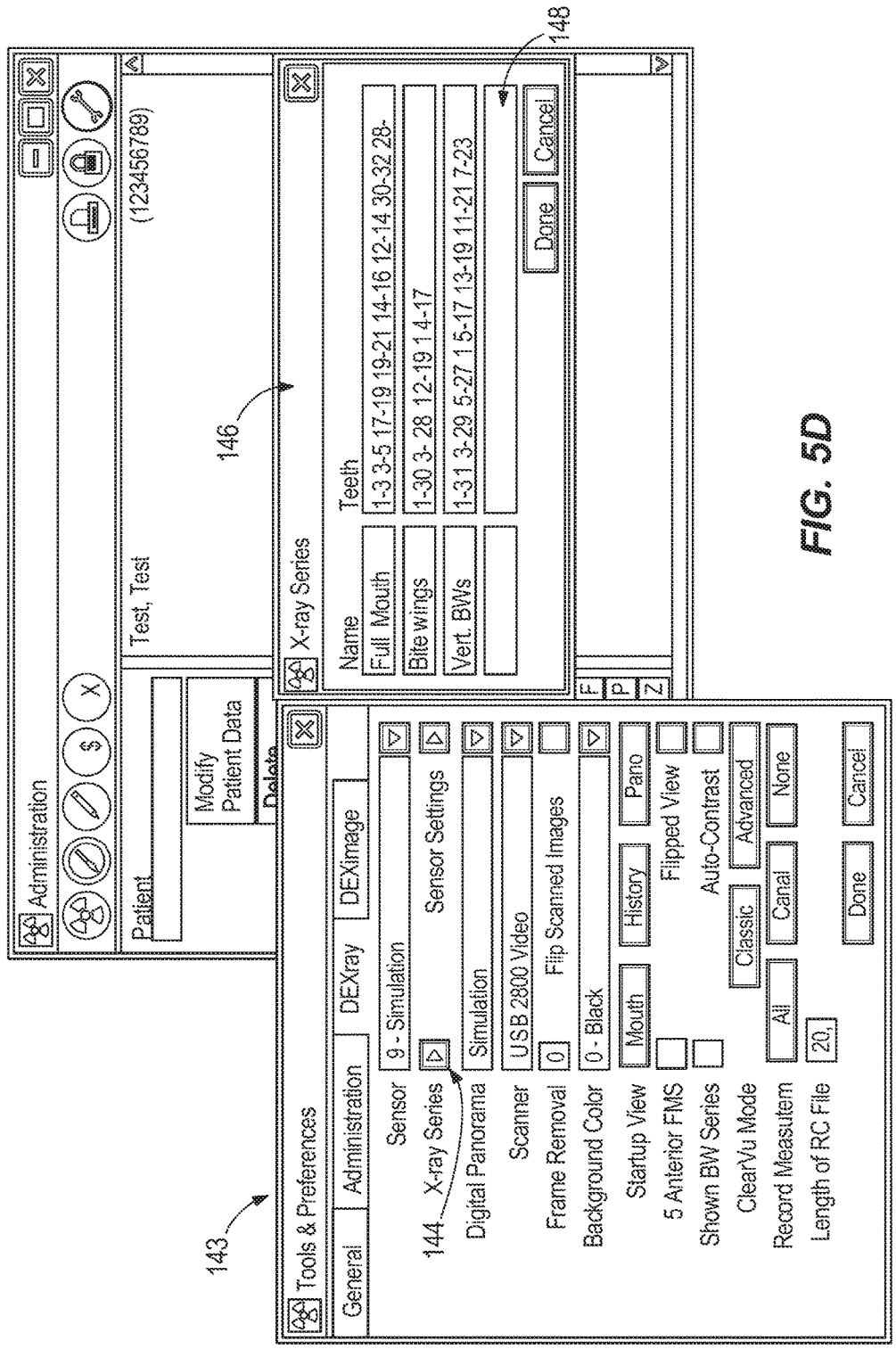
Figure 5E:
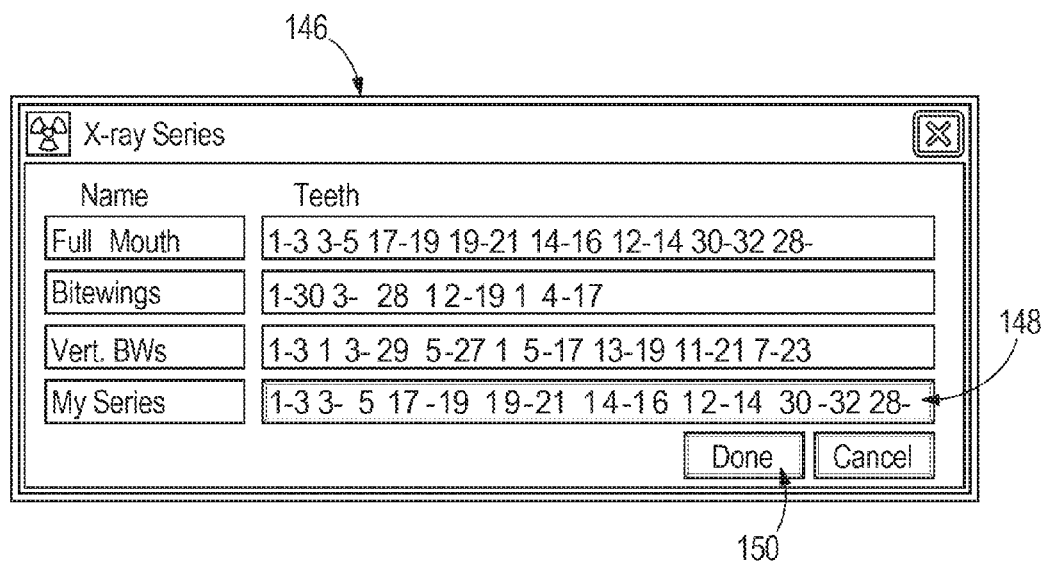
Figure 5F:
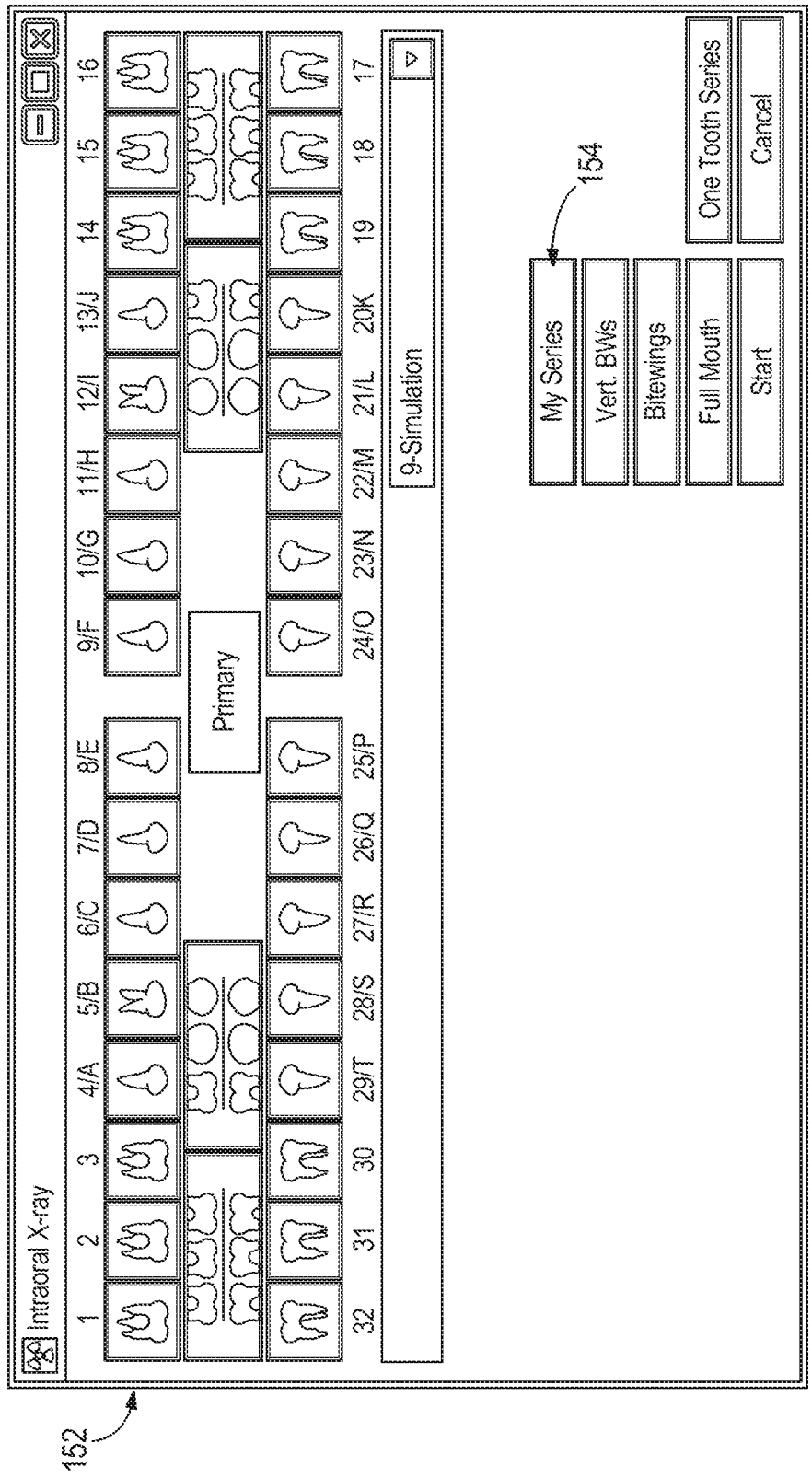

Also, in some embodiments, the x-ray unit (i.e., the controller 18) is configured to receive image characteristic information from sources other than the image processing unit 40. For example, as illustrated in FIG. 5B, an operator can initiate a predefined scan sequence or specify a customized scan sequence using the user interface 21 (at 140). For example, as illustrated in FIG. 5C, to create a customized scan sequence, an operator can select an icon 142 on the user interface 21 to access tools and preferences for the system 10. The user interface 21 can then display a "Preferences" tab 143 (see FIGS. 5C and 5D). From the "Preferences" tab, an operator can select an "x-ray series" button (e.g., an arrow) 144. Selecting this icon causes the user interface 21 to display an "x-ray series" window 146. As illustrated in FIG. 5E, using an empty field 148 within the window 146, an operator can enter a custom series name and custom tooth numbers (e.g., with a space between each number). When finished, the operator can select a "done" button 150. Therefore, when an operator uses the user interface 21 to operate the system 10, a tooth map window 152 displayed on the user interface 21 includes the newly-created custom series (see button 154 in FIG. 5F).

Accordingly, returning to FIG. 5B, the controller 18 receives the operator selections as the image characteristic information from the user interface 21 and uses the image characteristic information to identify the exposure parameters for each image in the sequence (e.g., using the data table(s) described above) (at 160). The controller 18 then applies the identified parameters as it controls the x-ray source 12 (at 162), which may also be based on other commands or data received from the operator, such as a start or stop command from a remote switch (at 164). The receptor 30 acquires image data as the x-ray source 12 emits radiation and sends the acquired image data to the image processing unit 40 for further processing and storage (at 166).

Alternatively or in addition, the image processing unit 40 can be configured to automatically identify a particular image being acquired based on the holder used for the receptor 30. For example, as described above, different holders are used to acquire different images (e.g., bitewing, posterior, anterior, endodontic, etc.). Accordingly, because the image processing unit 40 is connected to the receptor 30, the receptor 30 can be configured to identify the type of holder being used and forward this information to the image processing unit 40. The image processing unit can use the information from the receptor 30 to identify the type of image being acquired, and can provide image characteristic information to the x-ray unit based on the identified image type.

Figure 6:
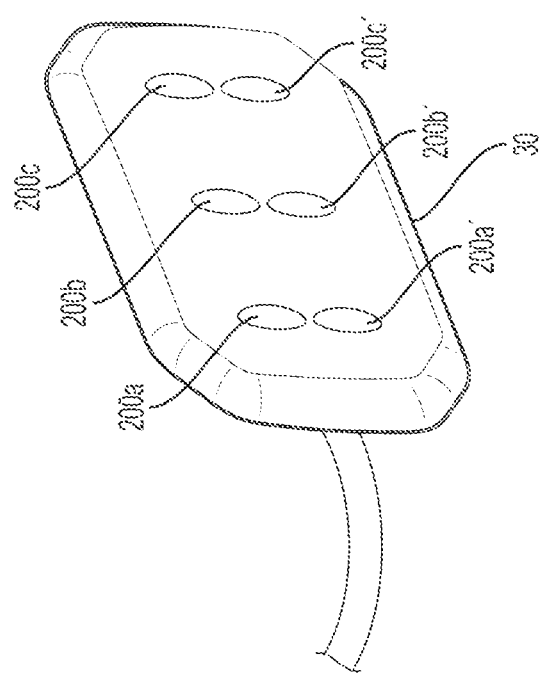
FIG. 6 illustrates a receptor used in the x-ray system of FIG. 1A or 2.
Figure 7:
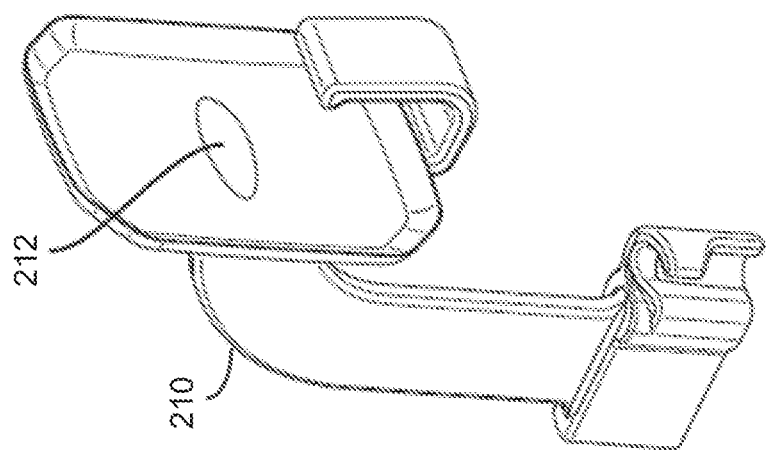
FIG. 7 illustrates a holder for the receptor of FIG. 6.
Figure 8:
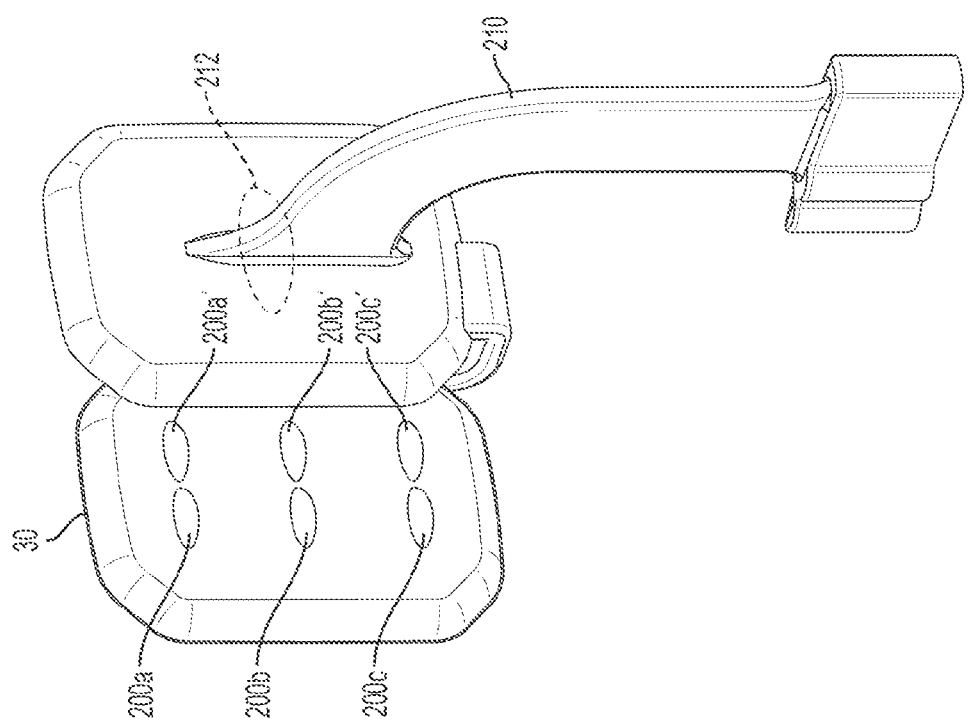
FIGS. 8-12 illustrate different receptor holders used in the x-ray system of FIG. 1A or 2.

For example, FIG. 6 illustrates a receptor 30. The receptor 30 includes a plurality of electrical pins or contacts 200. In some embodiments, the receptor 30 includes three pairs of contacts 200*a* and 200*a*', 200*b* and 200*b*', and 200*c* and 200*c*'. However, it should be understood that fewer or more contacts can also be used (e.g., to account for a smaller or larger number of different holders), and the contacts 200 can be arranged in different arrangements than as illustrated in FIG. 6. During use, the receptor 30 is placed within a holder. The holder also includes one or more electrical contacts that align with one or more of the contacts 200. The contact in the holder creates an electrical path between at least one of the pairs of contacts in the receptor 30 to complete an electrical circuit. Accordingly, using the electrical signal provided through the completed electrical circuit, the number and arrangement of the contacts of the holder that align with and engage with contacts 200 of the receptor 30 can be identified and used by receptor 30, and ultimately, the image processing unit 40, to identify the image being acquired. For example, FIG. 7 illustrates a bitewing holder 210. The bitewing holder 210 includes a single electrical contact 212. As illustrated in FIG. 8, the contact 212 of the holder 210 aligns with middle contacts 200*b* and 200*b*' of the receptor 30. Therefore, when the receptor 30 detects an electrical connection at the middle contacts 200*b* and 200*b*' but not the other pairs of contacts 200*a* and 200*a*' and 200*c* and 200*c*', the unit 40 identifies that a bitewing holder 210 is being used, and, consequently, a bitewing image is being taken. After identifying that a bitewing image is being taken, the image processing unit 40 can use a data table as described above to identify the exposure settings relating to a bitewing image.

Figure 9:
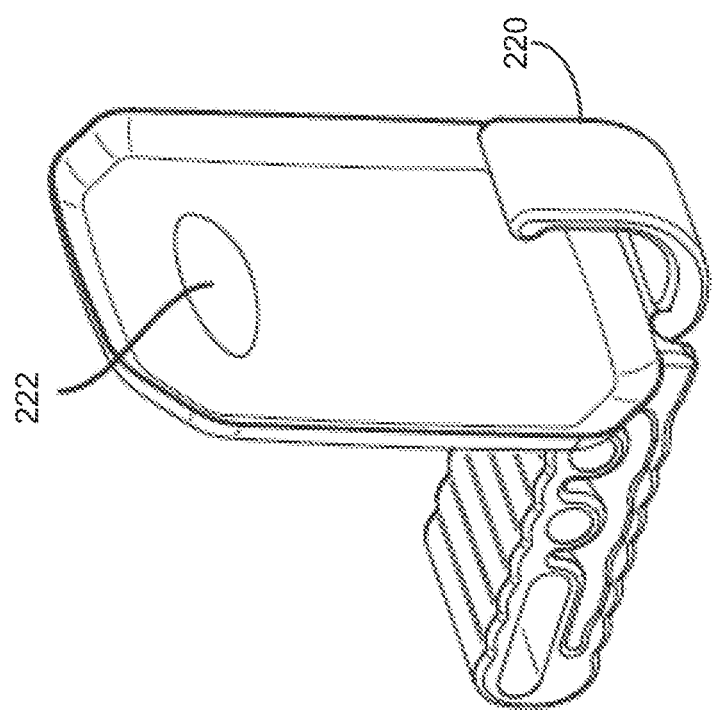

Similarly, as illustrated in FIG. 9, an anterior holder 220 includes a single electrical contact 222 that aligns with the contacts 200*c* and 200*c*' of the receptor 30. Therefore, when the receptor 30 detects an electrical connection at the contacts 200*c* and 200*c*' but not at the other pairs of contacts 200*a* and 200*a*' and 200*b* and 200*b*', the unit 40 identifies that an anterior holder 220 is being used, and, consequently, an anterior image is being taken.

Figure 10:
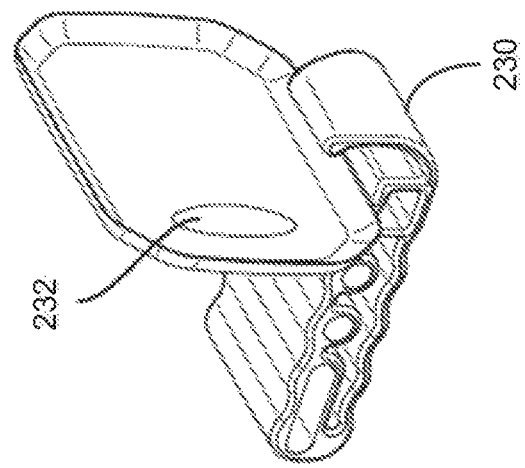

FIG. 10 illustrates a posterior holder 230. The posterior holder 230 includes a single electrical contact 232 that aligns with the contact 200*a* and 200*a*' of the receptor 30. Accordingly, when the receptor 30 detects an electrical connection at the contacts 200*a* and 200*a*' but not at the other pairs of contacts 200*b* and 200*b*' and 200*c* and 200*c*', the image processing unit 40 identifies that a posterior holder 230 is being used and, consequently, a posterior image is being taken.

Figure 11:
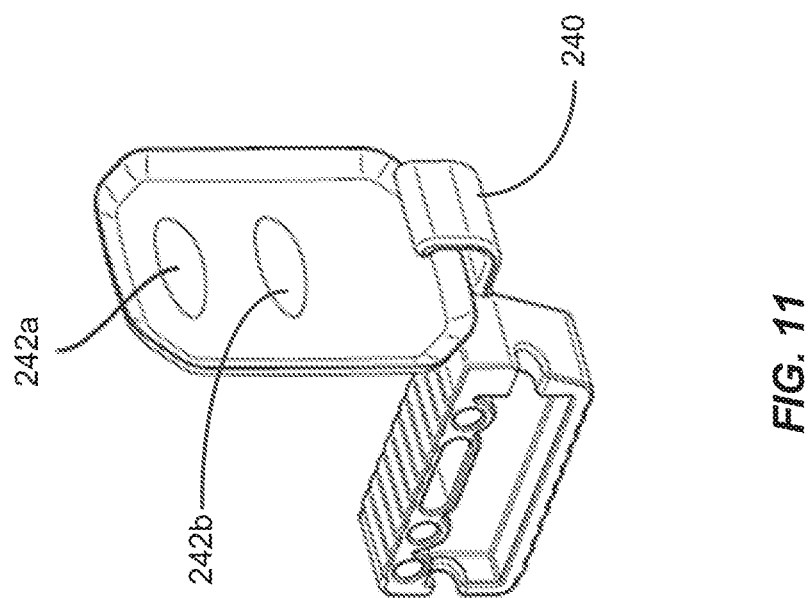
Figure 12:
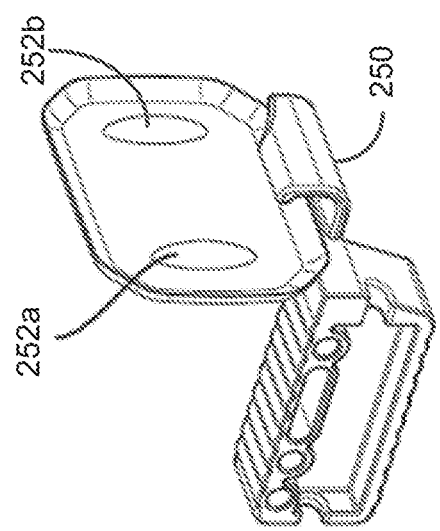

FIG. 11 illustrates an endodontic vertical holder 240. The endodontic vertical holder 240 includes two contacts 242*a* and 242*b* that align with the contacts 200*b* and 200*b*' and 200*c* and 200*c*' of the receptor 30. Accordingly, when the receptor 30 detects an electrical connection at the contacts 200*b* and 200*b*' and 200*c* and 200*c*' but not at contact 200*a*, the image processing unit 40 identifies that an endodontic vertical holder 240 is being used and, consequently, an endodontic image is being taken. Similarly, FIG. 12 illustrates an endodontic horizontal holder 250. The endodontic horizontal holder 250 includes two contacts 252*a* and 252*b* that align with the contacts 200*a* and 200*a*' and 200*c* and 200 *c*' of the receptor 30. Accordingly, when the receptor 30 detects an electrical connection at the contacts 200*a* and 200 *a*' and 200*c* and 200*c*' but not at contact 200*b* and 200*b*', the image processing unit 40 identifies that an endodontic horizontal holder 250 is being used and, consequently, an endodontic image is being taken.

Figure 13A:
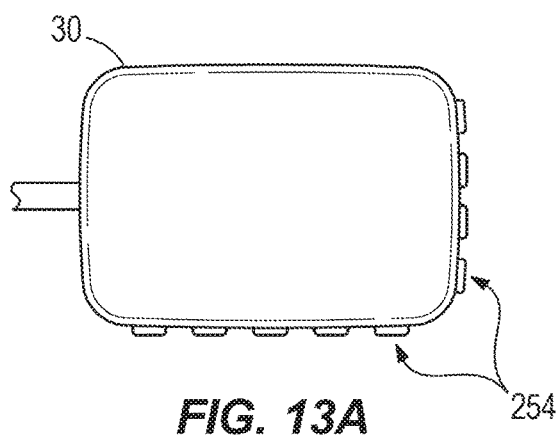
FIG. 13A is a top view of a receptor used in the x-ray system of FIG. 1A or 2, the receptor including a series of contacts on an outer edge.
Figure 13B:
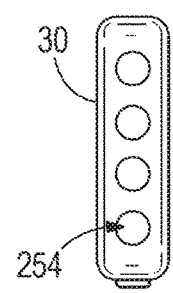
FIG. 13B is a side view of the receptor of FIG. 13A.
Figure 13C:
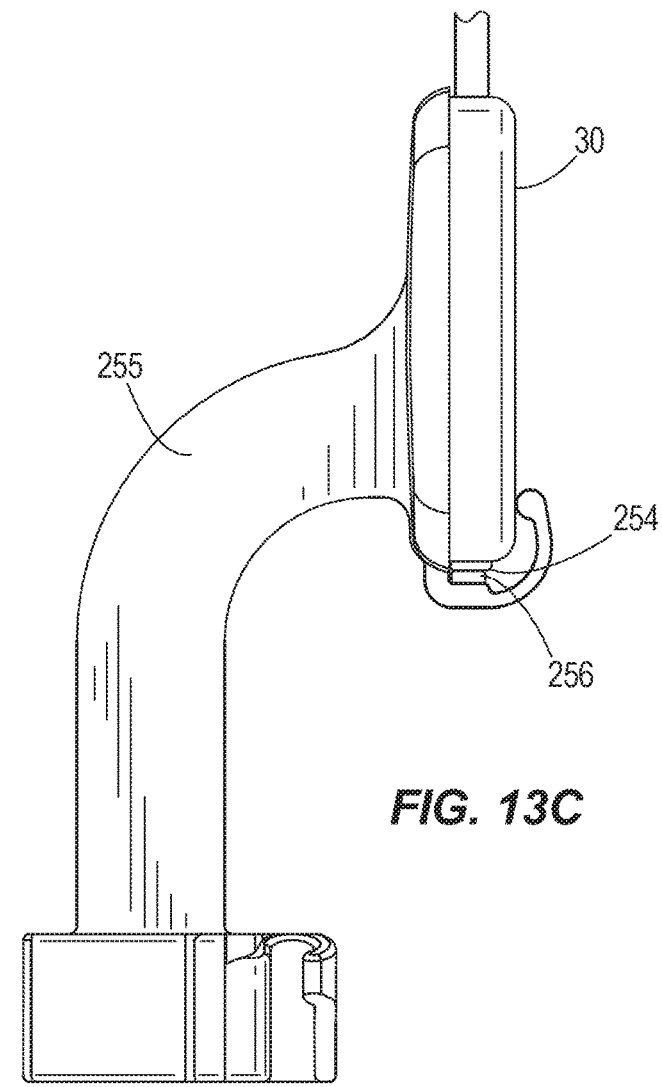
FIG. 13C is a side of the receptor of FIG. 13A mating with a receptor holder used in the x-ray system of FIG. 1A or 2.

It should be understood that the contacts illustrated in FIGS. 6-12 can be positioned at different locations on the receptor 30 and/or the holder and the position and orientation of the contacts illustrated in these figures is provided as one illustrative example. For example, in some embodiments, a series of contacts 254 can be placed on the outer edge(s) of a receptor 30 (see FIGS. 13A and 13B), and the corresponding holder 255 can have a contact strip 256 that will engage unique combinations of contacts 254 on the receptor 30 (see FIG. 13C). Accordingly, in this embodiment, the contacts 254 on each receptor 30 can be the same but different contacts 254 contact the contact strip 256 depending on the orientation or position of the receptor 30 and/or the holder 255 when the receptor 30 is mated with the holder 255 (and/or the type of holder 255 used with the receptor 30).

Figure 13D:
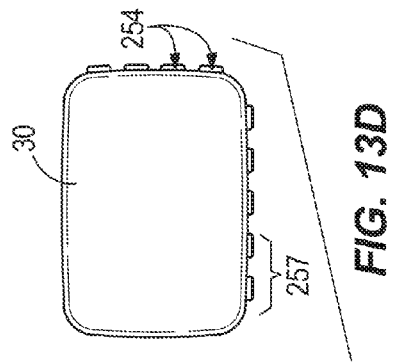
Figure 13E:
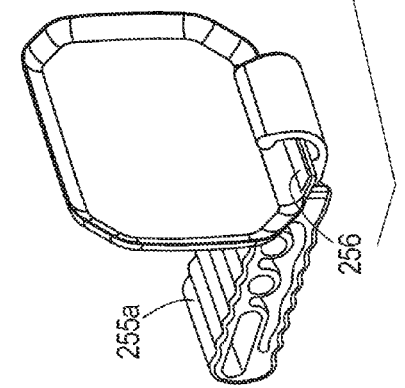
Figure 13G:
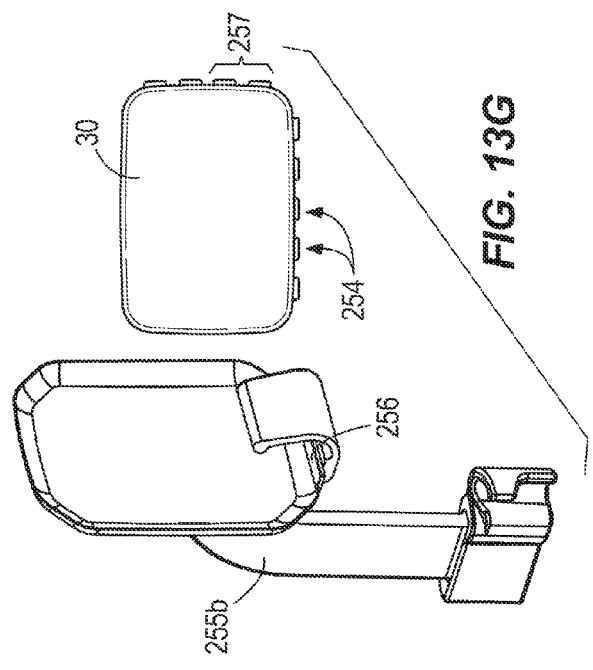
Figure 13F:
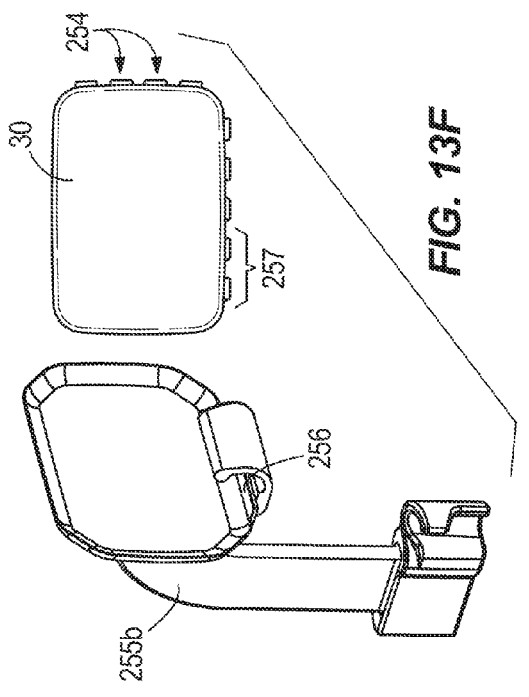

For example, FIGS. 13D and 13E illustrate two different orientations of a holder 255*a* (i.e., orientated as a posterior holder in FIG. 13D and orientated as an anterior holder in FIG. 13E). In each orientation, FIGS. 13D and 13E illustrate the particular contacts 254 of the receptor 30 that engage with the contact strip 256 on the holder 255*a* (engaging contacts are labeled as 257). Accordingly, because different contacts 254 engage with the contact strip 256 in each orientation, the type of image being taken can be identified based on the engaging contacts 257. Similarly, FIGS. 13F and 13G illustrate two different orientations of a bitewing holder 255*b* (i.e., orientated as a vertical bitewing holder in FIG. 13F and orientated as a horizontal bitewing holder in FIG. 13G). In each orientation, different contacts 254 of the receptor 30 engage with the contact strip 256 on the holder 255*b* (engaging contacts are labeled as 257). Likewise, FIGS. 13H and 13I illustrate two different orientations of an endodontic UL-LR holder 255*c* (i.e., a horizontal orientation in FIG. 13H and a vertical orientation in FIG. 13I) and the corresponding engaging contacts 257, and FIGS. 13J and 13K illustrate two different orientations of an endodontic LL-LR holder 255*d* (i.e., a horizontal orientation in FIG. 13J and a vertical orientation in FIG. 13K) and the corresponding engaging contacts 257.

Figure 14A:
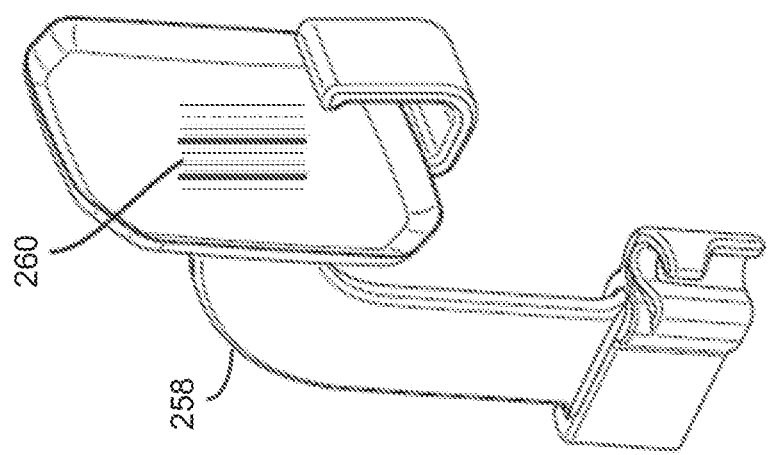
FIG. 14A illustrates a receptor holder used in the x-ray system of FIG. 1A or 2, the receptor including an optical or magnetic pattern.
Figure 14B:
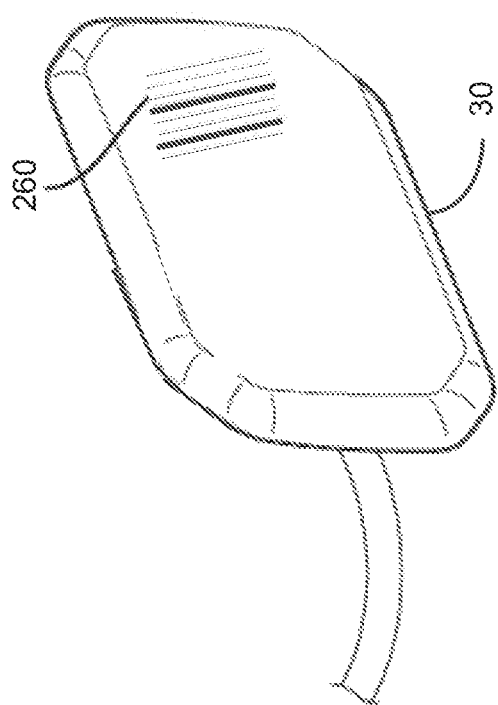
FIG. 14B illustrates a receptor used in the x-ray system of FIG. 1A or 2, the receptor including an optical or magnetic pattern.

It is to be understood that although the examples above use various patterns of electrical contacts to indicate the image type, the invention is not limited to the use of electrical contacts. Alternatively, or in addition, other kinds of indicator elements can be used. For example, as illustrated in FIG. 14A, a receptor holder 258 can contain a pattern 260, including for example an optical pattern (e.g., a 1D or 2D bar code), an arrangement of magnets, or patterned magnetic material, and the receptor 30 can include one or more detectors (e.g., optimal and/or magnetic sensors) to detect the pattern 260. In addition or alternatively, the pattern 260 can be disposed on the receptor 30 (see FIG. 14B), and the receptor holder 258 can include sensors (e.g., electrical, optical, and/or magnetic sensors) to detect the pattern 260. Optionally, the sensors on the receptor holder 258 can be arranged in a pattern indicating the kind of receptor holder.

A receptor 30 or receptor holder in accordance with the invention can also include one or more gravity sensors to indicate the orientation of the receptor 30 and holder with respect to the earth. This can be helpful, for example, to indicate whether the patient 31 is sitting upright, reclining, or lying down, which can resolve ambiguity as to which part of the mouth is being imaged if that is not apparent solely from the relative orientation of the sensor and the holder. The gravity sensors can comprise, for example, one or more 3-axis sensors.

Figure 15A:
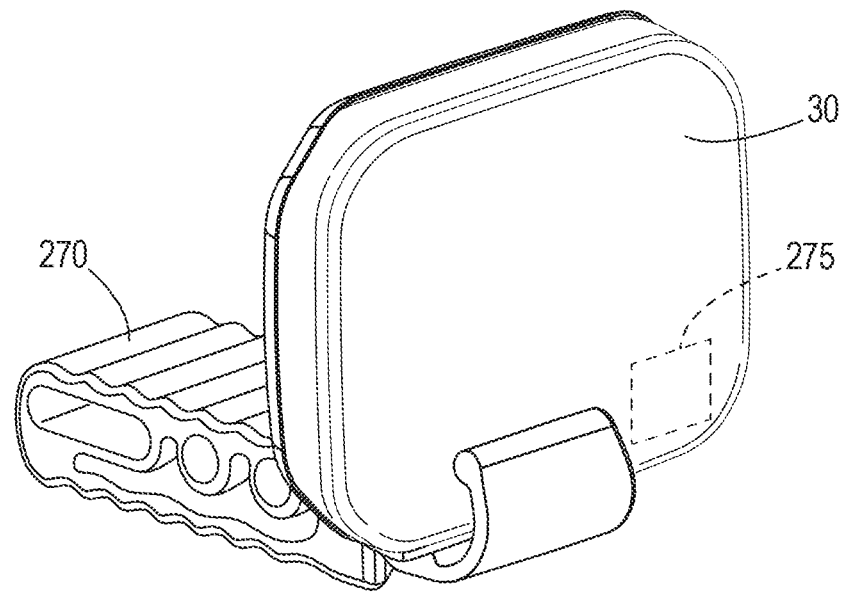
FIGS. 15A and B illustrate a holder and a receptor holder used in the x-ray system of FIG. 1A or 2, the receptor including a gravity sensor.
Figure 15B:
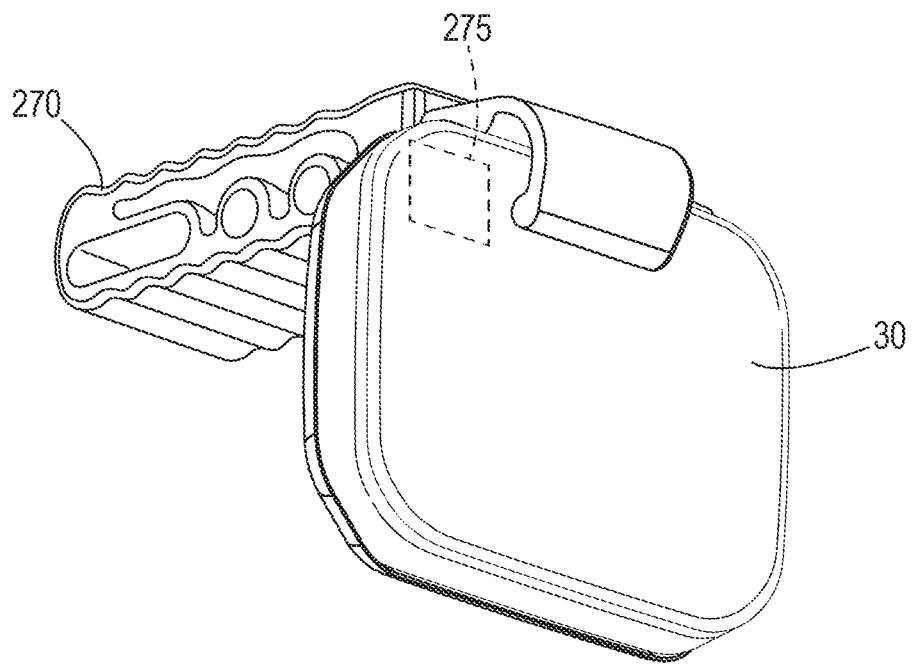

For example, when taking a full mouth series, contacts on the holder and receptor 30 can be used to identify which type of image is being taken. To identify if the upper or lower teeth are being imaged, a gravity sensor, for example as described in U.S. Pat. No. 7,775,713, incorporated by reference herein, could be used with the receptor 30 or the holder (see FIGS. 15A and 15B). As illustrated in FIGS. 15A and 15B, a receptor 30 can be connected to a holder 270 and can be used in a first position (see FIG. 15A) when taking images of upper teeth and can be used in a position (see FIG. 15B) when taking images of lower teeth. The receptor 30 can include a gravity sensor 275 that is used to detect a gravity value ("GV") to determine whether the holder 270 and the receptor 30 is positioned in the first position or the second position. As illustrated in FIGS. 15A and 15B, when a gravity sensor 275 is used, the receptor 30 can be keyed in the holder 270 (e.g., shaped to fit in only one orientation) or otherwise coupled to the holder in a consistent and precise manner to ensure that the receptor 30 is in the same position relative to the holder 270 every time it is used.

Figure 16A:
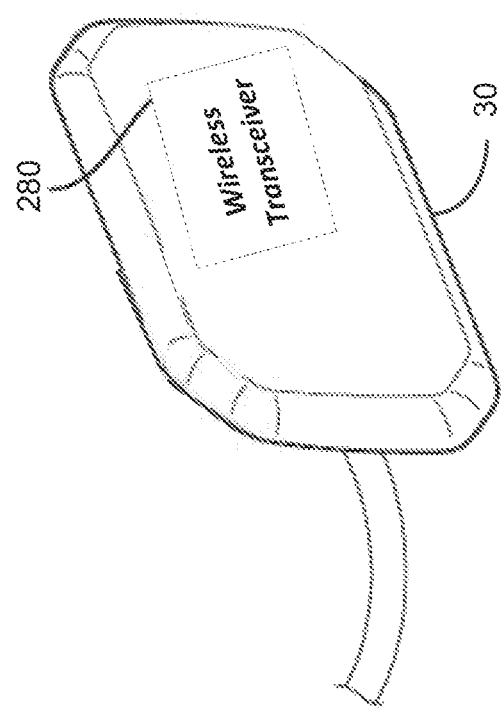
FIG. 16A illustrates a receptor used in the x-ray system of FIG. 1A or 2, the receptor including a wireless transceiver.
Figure 16B:
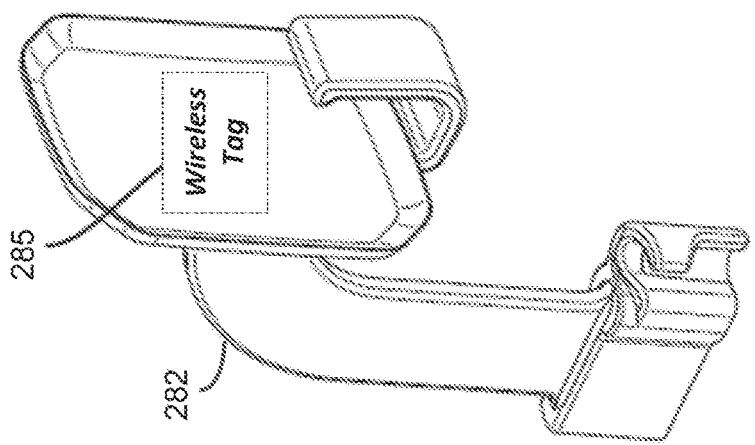
FIG. 16B illustrates a receptor holder used in the x-ray system of FIG. 1A or 2, the holder including a wireless tag detectable by the wireless transceiver included in the receptor of FIG. 16A.

In addition or alternatively, as illustrated in FIGS. 16A and 16B, a receptor 30 can include one or more wireless transceivers 280, including for example, a radio-frequency identification ("RFID") transceiver, a near-field communication ("NFC") transceiver, or other wireless transceivers, and a receptor holder 282 can include one or more wireless tags 285, including for example, a RFID tag, a NFC tag, or other wireless tags. Alternatively, or in addition, the wireless transceiver(s) 280 can be in the holder 282 and the wireless tag(s) 285 can be in the receptor 30, or both the receptor 30 and holder 282 can have one or more transceivers 280 and one or more tags 285. Furthermore, the wireless tag 285 can be either active (e.g., battery-powered) or passive. A wireless tag 285 on the receptor holder 282 can, for example, identify the kind of holder.

A wireless tag 285 can, but need not be, connected to a power source (e.g., the image processing unit 40) through a wire or cable, since it can also receive power wirelessly from the incoming electromagnetic (e.g., RF) signal. For example, a wireless tag 285 on the receptor holder can use the electromagnetic power that it receives from the transceiver 280 in the receptor 30 to charge a battery and/or power a microcontroller or other logic circuitry on or within the holder, in a manner similar to that used in the wireless identification and sensing platform ("WISP") technology. The logic circuitry can, for example, be connected to the contacts 212, optical sensors, magnetic sensors, gravity sensors, and/or other sensors on the receptor holder. By detecting the arrangement of electrical connections between the holder and the receptor, and/or by receiving signals from the various sensors in or on the receptor holder, the logic circuitry in/on the holder can determine the orientation of the receptor with respect to the holder and/or the orientation of the patient 31 and can transmit the orientation information back to the transceiver 280 in the receptor. The receptor 30 can then send the orientation information back to the image processing unit 40.

In addition, although the examples above use a cable 32 connected to the receptor 30 to transmit the image characteristic information to the image processing unit 40, the cable 32 can also be connected and transmit the image characteristic information: (1) from the receptor 30 to the x-ray controller 18, (2) from the receptor holder to the image processing unit 40, and/or (3) from the receptor holder to the x-ray controller 18.

Figure 17:
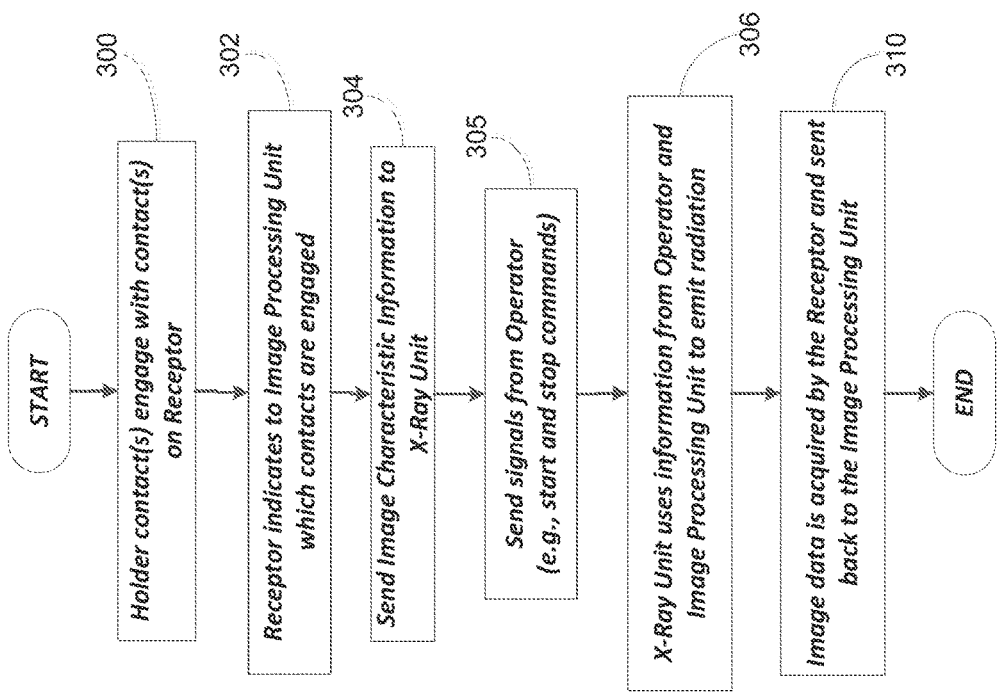
FIG. 17 is a flow chart illustrating another alternative method of automatically adjusting exposure parameters using receptor holders used in the x-ray system of FIG. 1A or 2.

FIG. 17 is a flowchart illustrating a method of automatically adjusting exposure parameters using the holders to identify a type of image being taken. As illustrated in FIG. 17, the receptor 30 is positioned in the holder such that the holder's contacts engage with contacts on the receptor 30 (at 300). The receptor 30 is configured to sense the engagements of one or more of the contacts and provide this information to the image processing unit 40 (at 302). The image processing unit 40 uses the information about the contacts to identify the type of holder being used and, consequently, the type of image being taken. The image processing unit 40 then sends image characteristic information to the x-ray unit based on the identified image type (at 304). As noted above, the image characteristic information can include exposure parameters or an identifier of a particular image type or image sequence.

Upon receiving the image characteristic information, the controller 18 controls the x-ray source 12 based on the image characteristic information provided by the image processing unit 40 and any signals or commands received from the operator (e.g., start and stop commands from a remote switch) (at 305) to emit appropriate radiation (at 306). The receptor 30 then acquires image data and forwards the image data to the image processing unit 40 (at 310). The image processing unit 40 can process the image data to generate an image and, optionally, display the generated image on a display device 43. It should be understood that in some embodiments, the receptor 30 can communicate image characteristic information (e.g., based on the electrical contacts) directly to the controller 18 rather than through the image processing unit 40. In addition, the information provided by the receptor 30 regarding the contacts can also be used (e.g., by the image processing unit 40 and/or the controller 18) to map acquired images to a proper location within a tooth map (see, e.g., FIG. 4) or otherwise store metadata with the acquired image regarding the type of the image. Accordingly, the automatic detection of the image type through the use of the electrical contacts allows the image processing unit 40 and/or the controller 18 to automatically categorize an image, which results in improved data management and overall patient service. Similarly, the image processing unit 40 and/or the controller 18 can be configured to generate a warning if the holder and an image selected by the operator do not match. For example, if the operator requests acquisition of a bitewing image but the receptor 30 detects engagement of electrical contacts associated with an endodontic holder, the image processing unit 40 and/or the controller 18 can generate a visual or audible warning to the operator.

Figure 18:
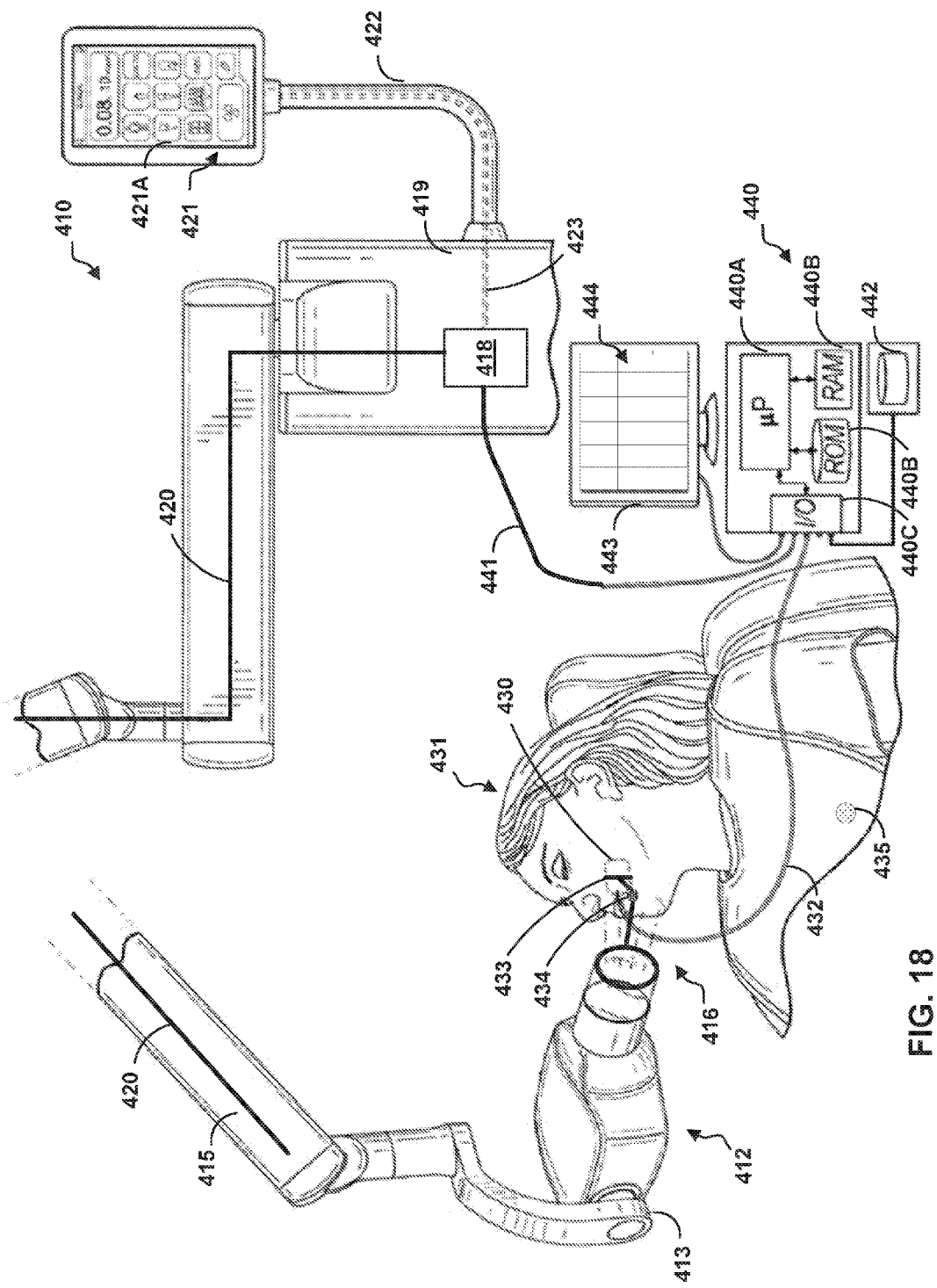
FIG. 18 schematically illustrates a dental x-ray system.

FIG. 18 is a schematic view of a dental x-ray system 410. The system 410 has some similarities to the system 10 of FIG. 2. The system 410 includes an x-ray source 412. In the embodiment illustrated the x-ray source 412 is located at an end 413 of a mechanical arm 415 and generates an x-ray stream 416. The system 410 also includes a controller 418, a housing 419, a connection 420, a user interface 421, a touchscreen 421A, a separate extension 422, a connection 423, a connection 432, an image processing unit 440, a processing unit 440A, memory modules 440B, an input/output interface 440C, and an external storage device 442. A display device 443 displays an image 444. Since these components of system 410 are similar to the components in system, 10 they will not be described in greater detail. Additionally, the system 410 includes an intraoral dental imaging sensor 430 which is designed to be placed inside the mouth of a patient 431. The dental imaging sensor 430 is held by a holder 433. As will be described in greater detail, a magnet 434 and a reference magnet 435 are used to help determine an orientation of the holder 433 and dental imaging sensor 430. Additionally, as will be described in greater detail a magnet 434 is used to help determine a type of the holder 433. In some embodiments, the intraoral dental imaging sensor 430 has some similarities to the receptor 30 and in some respects operates in a similar manner as the receptor 30.

As illustrated in FIG. 18, the x-ray source 412 is positioned (e.g., manually by an operator (not shown)) so that the x-ray stream 416 is directed toward an intraoral dental imaging sensor 430 located in the mouth of a patient 431. The intraoral dental imaging sensor 430 can include a digital detector or sensor. In some embodiments, the intraoral dental imaging sensor 430 includes an x-ray imaging sensor configured to sense x-ray energy, an accelerometer configured to sense changes in acceleration relative to gravity (e.g., a three axis accelerometer or other suitable accelerometer), and a magnetic field sensor configured to sense the magnetic field of a magnet (e.g., a three axis magnetic field sensor or other suitable sensor). In one embodiment, the magnetic field sensor is a Hall Effect sensor. In the example of FIG. 18, a wire, electric cable, fiber-optic cable, or similar connection 432 communicatively connects the intraoral dental imaging sensor 430 to an image processing unit 440. The connection 432 between the intraoral dental imaging sensor 430 and the image processing unit 440 can also be a wireless connection or other connection suitable for transmitting data between the devices. In some embodiments, the connection 432 also provides an electrical return path that allows electrical signals to be provided to and/or received from the intraoral dental imaging sensor 430 and/or a holder 433 for the intraoral dental imaging sensor 430. In other embodiments, a separate connection (e.g., a separate wire) from the connection 432 is used to provide the electrical signals. Although, the x-ray source 412 is illustrated as a wall-mounted unit, it is understood that the x-source 412 may also be a handheld portable unit (e.g., the NOMAD™ handheld x-ray system available from Aribex, Inc.).

The holder 433 for the intraoral dental imaging sensor 430 helps to align the x-ray stream 416 and the intraoral dental imaging sensor 430. The holder 433 for the intraoral dental imaging sensor 430 is configured to position and support the intraoral dental imaging sensor 430 in the mouth of the patient 431. The holder 433 illustrated in FIG. 18 is one example of one type of an imaging sensor holder.

The holder 433 may be configured as an upper posterior holder, a bitewing holder, a lower posterior holder, an upper anterior holder, a lower anterior holder, or other suitable holder. In some instances, the holder 433 may be configured so that it may be used interchangeably as an upper posterior holder, a bitewing holder, a lower posterior holder, an upper anterior holder, or a lower anterior holder. For example, the holder 433 may be a universal holder that can be used for all positions. In some embodiments, the holder 433 includes a bar that rotates or changes position relative to the holder. In this way, the holder 433 is a universal holder system that can be used for all positions.

As is discussed in greater detail below, the holder 433 may be placed at one of a plurality of posterior positions, a plurality of anterior positions, or a plurality of bitewing positions in the mouth of the patient 431. Therefore, the holder 433 may be used to position and support the intraoral dental imaging sensor 430 at a plurality of positions. For example, the upper posterior holder type of the holder 433 positions the intraoral dental imaging sensor 430 at one of the plurality of upper posterior positions in the mouth of the patient 431. Likewise, the lower posterior holder type of the holder 433 positions the intraoral dental imaging sensor 430 at one of the plurality of lower posterior positions in the mouth of the patient 431. The upper and lower anterior type and the bitewing type of the holder 433 may also position the intraoral dental imaging sensor 430 at one of a plurality of positions. In some embodiments, the holder 433 may be any of the holders (e.g., receptor holders) as described in FIGS. 5-16 or illustrated in FIGS. 7-12, 13C-13J, 14A, 15A, 15B, and 16B.

In the embodiment illustrated in FIG. 18, the holder 433 includes a magnet 434 attached to or located within the housing of the holder 433 and separate from a reference magnet 435 that is configured to be disposed on the patient 431. In other embodiments, the magnet 434 is positioned at other locations of the holder 433. In certain embodiments, the holder 433 can be a universal holder and the magnet 434 may be located on the bar or the bite block of the holder 433. In other embodiments, the magnet 434 is part of the bar (e.g., the bar can be made of magnetic material). It should be understood that even though the reference magnet 435 is illustrated as attached to the patient 431, the reference magnet 435 may be attached to other objects and placed at different locations (as long as there is sufficient distinction between the field generated by the magnet 434 and the reference magnet 435) including, for example, the holder 433. In some embodiments, the position of the magnet 434 attached to or part of holder 433 is correlated to the type of the holder 433. In other embodiments, the type of the magnet 434 is correlated to the type of the holder 433. For example, a magnetic material of the magnet 434 with a particular magnetic field strength and or location can be correlated to a particular the type of the holder 433. While a magnet of a different magnetic field strength and or location can be correlated to a different particular type of the holder 433. Accordingly, a characteristic of the magnet 434 (e.g., the position and/or the magnetic field strength) is indicative of the type of the holder 433. It is also understood that a lack of the magnet 434 may be used to differentiate between the types of the holder 433. In one example, the anterior type of the holder 433 does not include the magnet 434 and the lack of the magnet 434 indicates the anterior type of the holder 433. Of course, variations of this example are possible.

In certain embodiments, the reference magnet 435 is configured to differentiate between a plurality of posterior positions, a plurality of anterior positions, and a plurality of bitewing positions in the mouth of the patient 431. For example, the reference magnet 435 is used to differentiate between any of the positions of the intraoral dental imaging sensor 430. That is, a magnetic field of the reference magnet 435 provides a reference point or indication to the intraoral dental imaging sensor 430 or the image processing unit 440 to differentiate between any of the positions of the intraoral dental imaging sensor 430. Accordingly, a characteristic of the reference magnet 435 (e.g., the position and/or magnetic field strength) is indicative of whether the intraoral dental imaging sensor 430 is located in one of a plurality of posterior positions, a plurality of anterior positions, and a plurality of bitewing positions in the mouth of the patient 431. In some embodiments, the reference magnet 435 is positioned along the midline of the face of the patient 431.

It is understood that information (e.g., magnetic field data) regarding a position of the reference magnet 435 by itself may be used to distinguish between posterior, anterior, and bitewing positions. A user of the system 410 can attach the reference magnet 435 at a specific location on the patient 431 and use the magnetic field sensor of the intraoral dental imaging sensor 430 to detect the magnetic field of the reference magnet 435. The information regarding the magnetic field of the reference magnet 435 detected by the intraoral dental imaging sensor 430 can be used to calibrate the position of the intraoral dental imaging sensor 430. Upon calibrating the position of the intraoral dental imaging sensor 430, the image processing unit 440 can detect the type of the holder 433 using spatial information (e.g., use magnetic field direction) associated with the strength and/or direction of the magnetic field of the reference magnet 435. Upon determining the type of the holder 433, the image processing unit 440 can also use the spatial information associated with the strength and/or direction of the magnetic field of the reference magnet 435 to determine the exact position of the intraoral dental imaging sensor 430 in the mouth of the patient 431. For example, after calibration the image processing unit 440 can use the spatial information associated with the magnetic field of the reference magnet 435 to determine that the holder 433 is a bitewing holder and positioned in the front left part of the mouth of the patient 431 as described in FIG. 25 below.

It is also understood that information (e.g., magnetic field data or orientation data) regarding a position of the reference magnet 435, a position of the holder magnet 434, an orientation of the housing of the intraoral dental imaging sensor 430, or some combination thereof to distinguish between a posterior, anterior, and bitewing positions. For ease of understanding, the systems, methods, and devices as described below for distinguishing between the positions of the intraoral dental imaging sensor 430 include a combination of information from the accelerometer, the holder magnet 434, and the reference magnet 435. However, it is appreciated that the systems, methods, and devices as described below may only use the information from the reference magnet 435 to distinguish between the positions of the intraoral dental imaging sensor 430.

Figure 19:
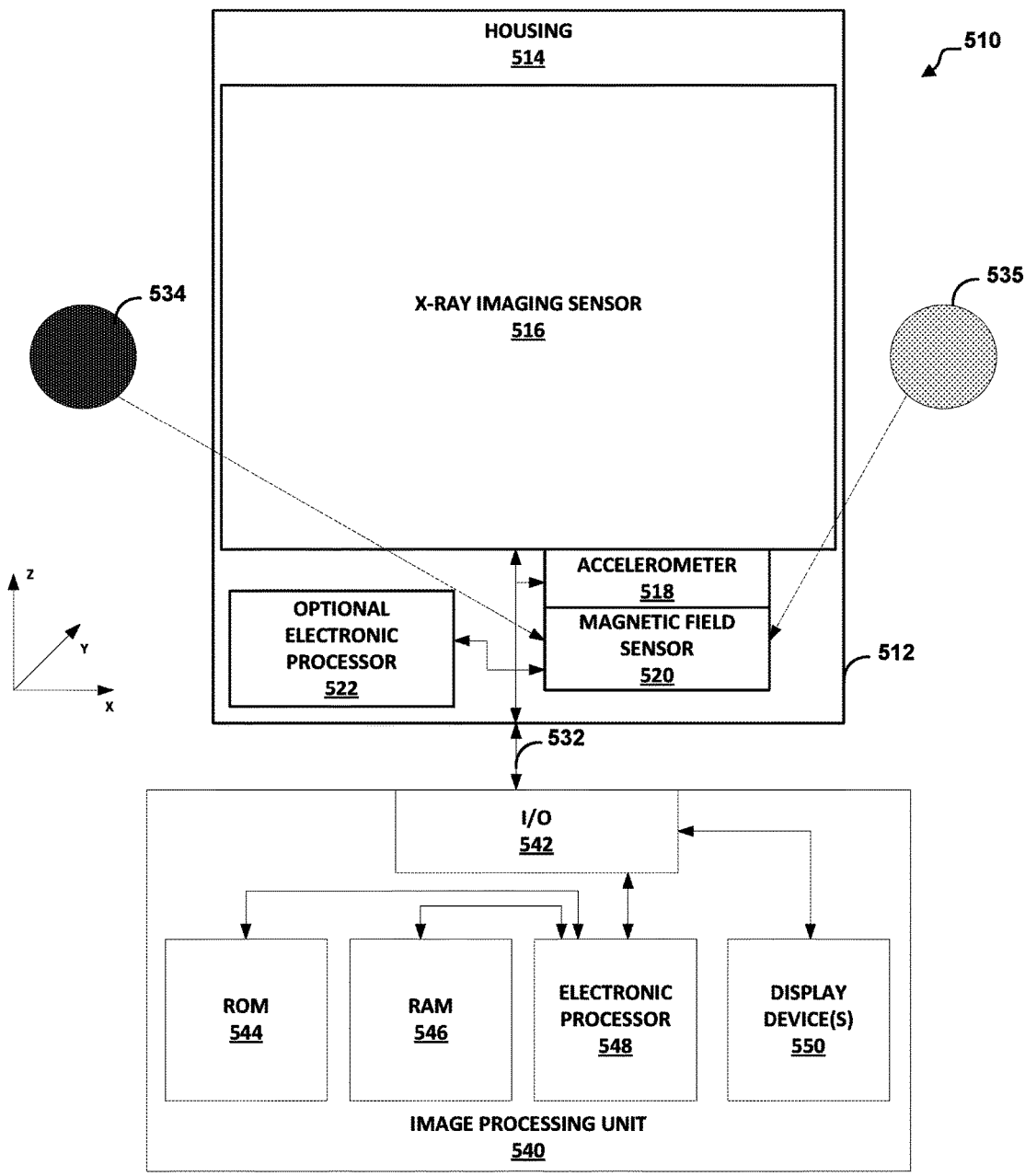
FIG. 19 is a block diagram of a dental x-ray system.

FIG. 19 is a block diagram of a dental x-ray system 510. The system 510 includes some components that are similar to some components of the system 410 of FIG. 18. In particular, the system 510 includes an intraoral dental imaging sensor 512 that is similar in some respects to the intraoral dental imaging sensor 430. The system 510 also includes an image processing unit (discussed below) that is similar to the image processing unit 440. In the example of FIG. 19, the system 510 includes the intraoral dental imaging sensor 512, a magnet 534, a reference magnet 535, and an image processing unit 540. The intraoral dental imaging sensor 512 includes a housing 514, an x-ray imaging sensor 516, an accelerometer 518, a magnetic field sensor 520, and an optional electronic processor 522. The image processing unit 540 includes input/output (I/O) interface 542, read-only memory (ROM) 544, read access memory (RAM) 546, electronic processor 548, and display device(s) 550. The magnet 534, the reference magnet 535, and the image processing unit 540 are similar to the magnet 434, the reference magnet 435, and the image processing unit 440 described above. As a consequence, these components will not be described again in greater detail. The intraoral dental imaging sensor 512 is similar in some respects to the intraoral dental imaging sensor 430 as described above and will be described in greater detail below.

The x-ray imaging sensor 516, the accelerometer 518, and the magnetic field sensor 520 of the intraoral dental imaging sensor 512 generate and output electrical signals that are indicative of x-ray image data, orientation data, and magnetic field data, respectively. The x-ray imaging sensor 516 is configured to receive x-rays and output image data over connection 532 to image processing unit 540. The accelerometer 518 is configured to detect an orientation of the housing 514 of the intraoral dental imaging sensor 512 and output orientation data over connection 532 to image processing unit 540. For example, the accelerometer 518 can be a three-dimensional accelerometer that can detect the orientation of the housing 514 in the x, y, and z directions with respect to the earth's gravitational field. The magnetic field sensor 520 is configured to sense one or more magnetic fields and output magnetic field data to the image processing unit 540 over connection 532. For example, the magnetic field sensor 520 can be a three-dimensional microelectromechanical (MEMS) based sensor that can detect the magnetic fields of the magnet 534 and the reference magnet 535 in the x, y, and z directions. The electrical signals are used by the image processing unit 540 and/or the intraoral dental imaging sensor 512 to determine the location and/or orientation of the intraoral dental imaging sensor 512, and/or the manner in which the sensor 512 is being used—e.g., which part of the patient's mouth is being imaged. For example, and as is explained below in more detail, the electrical signals can be used to indicate what image in a sequence of images is being acquired using the system 510. In this way, the sequence of images can be organized to conform to a specific sequence even when the images are taken out of order. In another example, the electrical signals can be used to indicate a type of the holder 433 as described above. In some embodiments, once the type of the holder 433 is determined from the electrical signals, the image processing unit 540 may indicate to a user on the display device 550 the type of positions and/or images that are possible with the type of the holder 433 determined from the electrical signals. For example, the image processing unit 540 may generate a graphical user interface that highlights the positions and/or images that are possible based on the type of the holder 433.

The image processing unit 540 includes one or more electronic processors 548 (hereinafter described as "an electronic processor 548"), which can be, for example, a microprocessor or an ASIC. It should be understood that the electronic processor 548 may include additional or different components (e.g., more than one electronic processor) than those components illustrated in FIG. 19 and may be configured to perform additional functionality than the functionality described herein.

In some embodiments, the electronic processor 548 is configured to receive the orientation data and the magnetic field data over the connection 532 and determine the position, orientation, and/or manner of usage of the intraoral dental imaging sensor 512 based at least in part on the orientation data or the magnetic field data. For example, the electronic processor 548 can determine the orientation of intraoral dental imaging sensor 512 relative to gravity based at least in part on the orientation data. In another example, the electronic processor 548 can determine a relative position of the intraoral dental imaging sensor 512 in the mouth of the patient based at least in part on the orientation data and the magnetic field data. In yet another example, the electronic processor 548 can determine a type of the holder 433 as described above based at least in part on the magnetic field data. In this example, the electronic processor 548 can also use the orientation data in addition to the magnetic field data to determine the type of the holder 433.

It should be understood that the intraoral dental imaging sensor 512 could be configured to carry out all or a portion of the processing carried out by the image processing unit 540. That is, in addition to or instead of determining the characteristics of the intraoral dental imaging sensor 512 in the electronic processor 548, the intraoral dental imaging sensor 512 may include one or more optional electronic processors 522 configured to determine the characteristics. In other words, the processing may be distributed between the intraoral dental imaging sensor 512 and the image processing unit 540 and even in other locations within the system 510 or at remote locations.

The image processing unit 540 also includes memory electrically coupled to the electronic processor 548. The memory may include one or more non-transitory memory modules, e.g., a ROM module 544 and a RAM module 546. The ROM module 544 and the RAM module 546 store software and data for processing image data collected by the intraoral dental imaging sensor 512 (e.g., to organize the images generated by the image processing unit 440 in a particular sequence). The ROM module 544 and the RAM module 546 also store image data and/or metadata associated with the image data (e.g., a log of exposure times, associated orientation data, associated magnetic field data, etc.). In addition, as described in more detail below, the ROM module 544 and the RAM module 546 store software and data for organizing the images in a particular sequence based at least in part on the position and/or orientation of the intraoral dental imaging sensor 512.

In some embodiments, the software stored on the ROM module 544 and the RAM module 546 includes the DEXIS Imaging Suite provided by Dental Imaging Technology Corp. In addition, the software stored on the ROM module 544 and the RAM module 546 may include instructions stored on a non-transitory computer-readable medium, that when executed are configured to cause an electronic processor 548 to perform a set of functions including receiving orientation data from the accelerometer 518 disposed in or on the housing 514 of the intraoral dental imaging sensor 512, receiving magnetic field data from a magnetic field sensor 520 disposed in or on the housing 514, determining the position, orientation, and/or manner of use of the intraoral dental imaging sensor 512 based at least in part on the orientation data, the magnetic field data, or both, and determining a type of the holder based at least in part on the magnetic field data. In this example, the instructions may include determining an orientation of the intraoral dental imaging sensor 512 relative to gravity based at least in part on the orientation data. Additionally or alternatively, in some embodiments, the instructions for determining the position of the intraoral dental imaging sensor 512 may include determining a relative position of the intraoral dental imaging sensor 512 in the mouth of the patient 431 based at least in part on the orientation data and the magnetic field data. Additionally or alternatively, in some embodiments, the electronic processor 548 receives image data from an x-ray imaging sensor 516 located in the housing 514 of the intraoral dental imaging sensor 512, generates images (e.g., image 444 as described above) from the image data, and organizes the images in a particular sequence (e.g., a full mouth series of images) based on the position and/or orientation of the intraoral dental imaging sensor 512 and the type of the holder.

In some embodiments, the input/output interface 542 also communicates with one or more external data storage devices (not shown) that store images acquired using the system 510, which can include cloud storage. As also illustrated in FIG. 19, the input/output interface 542 communicates with one or more display devices 550. The display device(s) 550 are used to display images acquired through use of the system 510. Image data, orientation data, and magnetic field data is processed by the image processing unit 540 to generate and organize a plurality of images in a particular sequence, and the images are sent to a display device 550 where the images can be viewed in the particular sequence (e.g., displayed as an image 444 as described above). In some embodiments, the display device(s) 550 include a touchscreen that receives input from an operator. The image processing unit 540 can also include one or more additional peripheral devices for receiving input from an operator (e.g., a keyboard, mouse, joystick, etc.).

As described in further detail below, the intraoral dental imaging sensor 512 can, for example, be located in eighteen different positions corresponding to a typical full-mouth series of images of the dentition of the patient, a partial mouth series comprising some subset of those eighteen positions, or images outside of the typical full-mouth series of images. To improve efficiency, a series of images may be taken by a user (for example, a dental technician) in any order. Additionally, the series of images may be taken by a user without requiring any knowledge of the type of the holder used to position the intraoral dental imaging sensor 512. Regardless of the lack of order or knowledge by the user, the image processing unit 540 outputs the different images in a particular sequence based at least in part on the orientation data and the magnetic field data. In some embodiments, image processing unit 540 may also be used to train a user to take the different images in a particular order. Similarly, in some embodiments, image processing unit 540 may also warn a user that one or more of the different images were taken out of a particular order.

FIGS. 20-23 are schematic views of an intraoral dental imaging sensor 430 and a bite block of a posterior holder 433A with a magnet 434A. FIGS. 20-23 are described from the perspective of the intraoral dental imaging sensor 430 and the image processing unit 440 as described above.

In the example of FIG. 20, the intraoral dental imaging sensor 430 is positioned by the bite block of posterior holder 433A at the upper posterior back left position within the mouth of the patient 431. In this example, the connection 432 exits at the upper right out of the mouth of the patient 431 as shown by the arrow indicating the orientation of the intraoral dental imaging sensor 430. Accordingly, the intraoral dental imaging sensor 430 can capture image data of the upper posterior back left position of the mouth of the patient 431 and transmit the image data to an image processing unit 440 over connection 432. As illustrated in FIG. 20, the magnet 434A attached to the bite block of the posterior holder 433A is positioned near the bottom left corner of the intraoral dental imaging sensor 430 opposite from the exit of the connection 432. Accordingly, the intraoral dental imaging sensor 430 or the image processing unit 440 may determine that the holder 433 is a posterior holder 433A on the upper left side based at least in part on data from an accelerometer and a magnetic field sensor. The accelerometer provides orientation data indicating the orientation of the intraoral dental imaging sensor 430 relative to gravity. For example, the orientation data indicates the exit of the connection 432 out of the mouth of the patient 431 is at the upper right corner. The magnetic field provides magnetic field data indicating the position of the magnet 434A, for example, the magnet 434A is at the bottom left corner opposite from the exit of the connection 432. Thereby indicating which holder is being used and that the sensor could be in the left posterior upper back or front, or right posterior lower front or back. The accelerometer data eliminates the ambiguity between the upper left and lower right posterior positions.

In the example of FIG. 21, the intraoral dental imaging sensor 430 is positioned by the bite block of the posterior holder 433A at the upper posterior front left position within the mouth of the patient 431. Compared to the intraoral dental imaging sensor 430 of FIG. 20, the intraoral dental imaging sensor 430 of FIG. 21 is oriented in the same manner, but positioned towards the front of the mouth of the patient 431. That is, the connection 432 exits at the upper right out of the mouth of the patient 431 as shown by the arrow indicating the orientation of the intraoral dental imaging sensor 430. Accordingly, the intraoral dental imaging sensor 430 can capture image data of the upper posterior front left position of the mouth of the patient 431 and transmit the image data to an image processing unit 440 over connection 432. As illustrated in FIG. 21, the magnet 434A attached to the bite block of the posterior holder 433A is positioned near the bottom left corner of the intraoral dental imaging sensor 430 opposite from the exit of the connection 432. Accordingly, the intraoral dental imaging sensor 430 or the image processing unit 440 may determine that the holder 433 is the posterior holder 433A on the upper left side based at least in part on data from an accelerometer and a magnetic field sensor. The accelerometer provides orientation data indicating the orientation of the intraoral dental imaging sensor 430. For example, the orientation data indicates the exit of the connection 432 out of the mouth of the patient 431 is at the upper right corner. The magnetic field provides magnetic field data indicating the position of the magnet 434A. For example, the magnet 434A is at the bottom left corner opposite from the exit of the connection 432.

In the example of FIG. 22, the intraoral dental imaging sensor 430 is positioned by the bite block of the posterior holder 433A at the upper posterior front right position within the mouth of the patient 431. Compared to the intraoral dental imaging sensor 430 of FIG. 20, the intraoral dental imaging sensor 430 of FIG. 22 is inverted, and positioned towards the front of the mouth of the patient 431. That is, the connection 432 exits at the bottom left of the mouth of the patient 431 as shown by the arrow indicating the orientation of the intraoral dental imaging sensor 430. Accordingly, the intraoral dental imaging sensor 430 can capture image data of the upper posterior front right position of the mouth of the patient 431 and transmit the image data to an image processing unit 440 over connection 432. As illustrated in FIG. 22, the magnet 434A attached to the bite block of the posterior holder 433A is positioned near the bottom left corner of the intraoral dental imaging sensor 430 at the same corner as the exit of the connection 432. Accordingly, the intraoral dental imaging sensor 430 or the image processing unit 440 may determine that the holder 433 is the posterior holder 433A based at least in part on data from an accelerometer and a magnetic field sensor. The accelerometer provides orientation data indicating the orientation of the intraoral dental imaging sensor 430. For example, the orientation data indicates the exit of the connection 432 out of the mouth of the patient 431 is at the bottom left corner. The magnetic field provides magnetic field data indicating the position of the magnet 434A. For example, the magnet 434A is at the bottom left corner near the exit of the connection 432.

In the example of FIG. 23, the intraoral dental imaging sensor 430 is positioned by the bite block of the posterior holder 433A at the upper posterior back right position within the mouth of the patient 431. Compared to the intraoral dental imaging sensor 430 of FIG. 20, the intraoral dental imaging sensor 430 of FIG. 23 is inverted and positioned towards the back of the mouth of the patient 431. That is, the connection 432 exits at the bottom left of the mouth of the patient 431 as shown by the arrow indicating the orientation of the intraoral dental imaging sensor 430. Accordingly, the intraoral dental imaging sensor 430 can capture image data of the upper posterior back right position of the mouth of the patient 431 and transmit the image data to an image processing unit 440 over connection 432. As illustrated in FIG. 23, the magnet 434A attached to the bite block of the posterior holder 433A is positioned near the bottom left corner of the intraoral dental imaging sensor 430 at the same corner as the exit of the connection 432. Accordingly, the intraoral dental imaging sensor 430 or the image processing unit 440 may determine that the holder 433 is the posterior holder 433A based at least in part on data from an accelerometer and a magnetic field sensor. The accelerometer provides orientation data indicating the orientation of the intraoral dental imaging sensor 430. For example, the orientation data indicates the exit of the connection 432 out of the mouth of the patient 431 is at the bottom left corner. The magnetic field provides magnetic field data indicating the position of the magnet 434A. For example, the magnet 434A is at the bottom left corner near the exit of the connection 432.

FIGS. 24-27 are schematic views of an intraoral dental imaging sensor 430 and a bite block of a bitewing holder 433B with a magnet 434B. FIGS. 24-27 are described with from the perspective of the intraoral dental imaging sensor 430 and the image processing unit 440 as described above.

In the example of FIG. 24, the intraoral dental imaging sensor 430 is positioned by the bite block of the bitewing holder 433B at the bitewing back left position within the mouth of the patient 431. In this example, the connection 432 exits at the upper right out of the mouth of the patient 431 as shown by the arrow indicating the orientation of the intraoral dental imaging sensor 430. Accordingly, the intraoral dental imaging sensor 430 can capture image data of the bitewing back left position of the mouth of the patient 431 and transmit the image data to an image processing unit 440 over connection 432. As illustrated in FIG. 24, the magnet 434B attached to the bite block of the bitewing holder 433B is positioned near the middle left side of the intraoral dental imaging sensor 430 opposite from the exit of the connection 432. Accordingly, the intraoral dental imaging sensor 430 or the image processing unit 440 may determine that the holder 433 is the bitewing holder 433B based at least in part on data from an accelerometer and a magnetic field sensor. The accelerometer provides orientation data indicating the orientation of the intraoral dental imaging sensor 430. For example, the orientation data indicates the exit of the connection 432 out of the mouth of the patient 431 is at the upper right corner. The magnetic field provides magnetic field data indicating the position of the magnet 434B. For example, the magnet 434B is at the middle left side opposite from the exit of the connection 432.

In the example of FIG. 25, the intraoral dental imaging sensor 430 is positioned by the bite block of the bitewing holder 433B at the bitewing front left position within the mouth of the patient 431. Compared to the intraoral dental imaging sensor 430 of FIG. 24, the intraoral dental imaging sensor 430 of FIG. 25 is oriented in the same manner, but positioned towards the front of the mouth of the patient 431. That is, the connection 432 exits at the upper right out of the mouth of the patient 431 as shown by the arrow indicating the orientation of the intraoral dental imaging sensor 430.

Accordingly, the intraoral dental imaging sensor 430 can capture image data of the bitewing front left position of the mouth of the patient 431 and transmit the image data to an image processing unit 440 over connection 432. As illustrated in FIG. 25, the magnet 434B attached to the bite block of the bitewing holder 433B is positioned near the middle left side of the intraoral dental imaging sensor 430 opposite from the exit of the connection 432. Accordingly, the intraoral dental imaging sensor 430 or the image processing unit 440 may determine that the holder 433 is the bitewing holder 433B based at least in part on data from an accelerometer and a magnetic field sensor. The accelerometer provides orientation data indicating the orientation of the intraoral dental imaging sensor 430. For example, the orientation data indicates the exit of the connection 432 out of the mouth of the patient 431 is at the upper right corner. The magnetic field provides magnetic field data indicating the position of the magnet 434B. For example, the magnet 434B is at the middle left side opposite from the exit of the connection 432.

In the example of FIG. 26, the intraoral dental imaging sensor 430 is positioned by the bite block of the bitewing holder 433B at the bitewing front right position within the mouth of the patient 431. Compared to the intraoral dental imaging sensor 430 of FIG. 24, the intraoral dental imaging sensor 430 of FIG. 26 is inverted, and positioned towards the front of the mouth of the patient 431. That is, the connection 432 exits at the bottom left of the mouth of the patient 431 as shown by the arrow indicating the orientation of the intraoral dental imaging sensor 430. Accordingly, the intraoral dental imaging sensor 430 can capture image data of the bitewing front right position of the mouth of the patient 431 and transmit the image data to an image processing unit 440 over connection 432. As illustrated in FIG. 26, the magnet 434B attached to the bite block of the bitewing holder 433B is positioned near the middle right side of the intraoral dental imaging sensor 430 opposite from the exit of the connection 432. Accordingly, the intraoral dental imaging sensor 430 or the image processing unit 440 may determine that the holder 433 is the bitewing holder 433B based at least in part on data from an accelerometer and a magnetic field sensor. The accelerometer provides orientation data indicating the orientation of the intraoral dental imaging sensor 430. For example, the orientation data indicates the exit of the connection 432 out of the mouth of the patient 431 is at the bottom left corner. The magnetic field provides magnetic field data indicating the position of the magnet 434B. For example, the magnet 434B is at the middle right side opposite from the exit of the connection 432.

In the example of FIG. 27, the intraoral dental imaging sensor 430 is positioned by the bite block of the bitewing holder 433B at the bitewing back right position within the mouth of the patient 431. Compared to the intraoral dental imaging sensor 430 of FIG. 24, the intraoral dental imaging sensor 430 of FIG. 27 is inverted and positioned towards the back of the mouth of the patient 431. That is, the connection 432 exits at the bottom left of the mouth of the patient 431 as shown by the arrow indicating the orientation of the intraoral dental imaging sensor 430. Accordingly, the intraoral dental imaging sensor 430 can capture image data of the bitewing back right position of the mouth of the patient 431 and transmit the image data to an image processing unit 440 over connection 432. As illustrated in FIG. 27, the magnet 434B attached to the bite block of the bitewing holder 433B is positioned near the middle right side of the intraoral dental imaging sensor 430 opposite from the exit of the connection 432. Accordingly, the intraoral dental imaging sensor 430 or the image processing unit 440 may determine that the holder 433 is the bitewing holder 433B based at least in part on data from an accelerometer and a magnetic field sensor. The accelerometer provides orientation data indicating the orientation of the intraoral dental imaging sensor 430. For example, the orientation data indicates the exit of the connection 432 out of the mouth of the patient 431 is at the bottom left corner. The magnetic field provides magnetic field data indicating the position of the magnet 434B. For example, the magnet 434B is at the middle right side opposite from the exit of the connection 432.

FIGS. 28-31 are schematic views of an intraoral dental imaging sensor 430 and a bite block of a posterior holder 433C with a magnet 434C. FIGS. 28-31 are described with from the perspective of the intraoral dental imaging sensor 430 and the image processing unit 440 as described above. In some embodiments, the posterior holder 433C is similar to the posterior holder 433A as described above.

In the example of FIG. 28, the intraoral dental imaging sensor 430 is positioned by the bite block of the posterior holder 433C at the lower posterior back left position within the mouth of the patient 431. In this example, the connection 432 exits at the upper right out of the mouth of the patient 431 as shown by the arrow indicating the orientation of the intraoral dental imaging sensor 430. Accordingly, the intraoral dental imaging sensor 430 can capture image data of the lower posterior back left position of the mouth of the patient 431 and transmit the image data to an image processing unit 440 over connection 432. As illustrated in FIG. 28, the magnet 434C attached to the bite block of the posterior holder 433C is positioned near the upper right corner of the intraoral dental imaging sensor 430 near the exit of the connection 432. Accordingly, the intraoral dental imaging sensor 430 or the image processing unit 440 may determine that the holder 433 is the posterior holder 433C based at least in part on data from an accelerometer and a magnetic field sensor. The accelerometer provides orientation data indicating the orientation of the intraoral dental imaging sensor 430. For example, the orientation data indicates the exit of the connection 432 out of the mouth of the patient 431 is at the upper right corner. The magnetic field provides magnetic field data indicating the position of the magnet 434C. For example, the magnet 434C is at the upper right corner near the exit of the connection 432.

In the example of FIG. 29, the intraoral dental imaging sensor 430 is positioned by the bite block of the posterior holder 433C at the lower posterior front left position within the mouth of the patient 431. Compared to the intraoral dental imaging sensor 430 of FIG. 28, the intraoral dental imaging sensor 430 of FIG. 29 is oriented in the same manner, but positioned towards the front of the mouth of the patient 431. That is, the connection 432 exits at the upper right out of the mouth of the patient 431 as shown by the arrow indicating the orientation of the intraoral dental imaging sensor 430. Accordingly, the intraoral dental imaging sensor 430 can capture image data of the lower posterior front left position of the mouth of the patient 431 and transmit the image data to an image processing unit 440 over connection 432. As illustrated in FIG. 29, the magnet 434C attached to the bite block of the posterior holder 433C is positioned near the upper right corner of the intraoral dental imaging sensor 430 near the exit of the connection 432. Accordingly, the intraoral dental imaging sensor 430 or the image processing unit 440 may determine that the holder 433 is the posterior holder 433C based at least in part on data from an accelerometer and a magnetic field sensor. The accelerometer provides orientation data indicating the orientation of the intraoral dental imaging sensor 430. For example, the orientation data indicates the exit of the connection 432 out of the mouth of the patient 431 is at the upper right corner. The magnetic field provides magnetic field data indicating the position of the magnet 434C. For example, the magnet 434C is at the upper right corner near the exit of the connection 432.

In the example of FIG. 30, the intraoral dental imaging sensor 430 is positioned by the bite block of the posterior holder 433C at the lower posterior front right position within the mouth of the patient 431. Compared to the intraoral dental imaging sensor 430 of FIG. 28, the intraoral dental imaging sensor 430 of FIG. 30 is inverted, and positioned towards the front of the mouth of the patient 431. That is, the connection 432 exits at the bottom left of the mouth of the patient 431 as shown by the arrow indicating the orientation of the intraoral dental imaging sensor 430. Accordingly, the intraoral dental imaging sensor 430 can capture image data of the lower posterior front right position of the mouth of the patient 431 and transmit the image data to an image processing unit 440 over connection 432. As illustrated in FIG. 30, the magnet 434C attached to the bite block of the posterior holder 433C is positioned near the upper right corner of the intraoral dental imaging sensor 430 opposite from the exit of the connection 432. Accordingly, the intraoral dental imaging sensor 430 or the image processing unit 440 may determine that the holder 433 is the posterior holder 433C based at least in part on data from an accelerometer and a magnetic field sensor. The accelerometer provides orientation data indicating the orientation of the intraoral dental imaging sensor 430. For example, the orientation data indicates the exit of the connection 432 out of the mouth of the patient 431 is at the bottom left corner. The magnetic field provides magnetic field data indicating the position of the magnet 434C. For example, the magnet 434C is at the upper right corner opposite from the exit of the connection 432.

In the example of FIG. 31, the intraoral dental imaging sensor 430 is positioned by the bite block of the posterior holder 433C at the lower posterior back right position within the mouth of the patient 431. Compared to the intraoral dental imaging sensor 430 of FIG. 28, the intraoral dental imaging sensor 430 of FIG. 31 is inverted and positioned towards the back of the mouth of the patient 431. That is, the connection 432 exits at the bottom left of the mouth of the patient 431 as shown by the arrow indicating the orientation of the intraoral dental imaging sensor 430. Accordingly, the intraoral dental imaging sensor 430 can capture image data of the lower posterior back right position of the mouth of the patient 431 and transmit the image data to an image processing unit 440 over connection 432. As illustrated in FIG. 31, the magnet 434C attached to the bite block of the posterior holder 433C is positioned near the upper right corner of the intraoral dental imaging sensor 430 opposite from the exit of the connection 432. Accordingly, the intraoral dental imaging sensor 430 or the image processing unit 440 may determine that the holder 433 is the posterior holder 433C based at least in part on data from an accelerometer and a magnetic field sensor. The accelerometer provides orientation data indicating the orientation of the intraoral dental imaging sensor 430. For example, the orientation data indicates the exit of the connection 432 out of the mouth of the patient 431 is at the bottom left corner. The magnetic field provides magnetic field data indicating the position of the magnet 434C. For example, the magnet 434C is at the upper right corner opposite from the exit of the connection 432.

Figures 32, 33, 34:
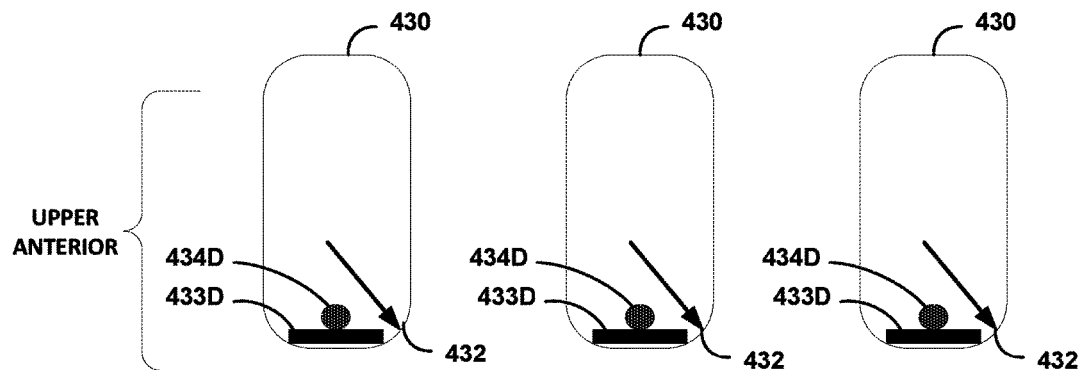
FIGS. 32-34 are schematic views of an intraoral dental imaging sensor and a bite block of an upper anterior holder with a magnet.

FIGS. 32-34 are schematic views of an intraoral dental imaging sensor 430 and a bite block of an anterior holder 433D with a magnet 434D. FIGS. 32-34 are described with from the perspective of the intraoral dental imaging sensor 430 and the image processing unit 440 as described above.

In the example of FIG. 32, the intraoral dental imaging sensor 430 is positioned by the bite block of the anterior holder 433D at the upper anterior left position within the mouth of the patient 431. In this example, the connection 432 exits at the bottom right out of the mouth of the patient 431 as shown by the arrow indicating the orientation of the intraoral dental imaging sensor 430. Accordingly, the intraoral dental imaging sensor 430 can capture image data of the upper anterior left position of the mouth of the patient 431 and transmit the image data to an image processing unit 440 over connection 432. As illustrated in FIG. 32, the magnet 434D attached to the bite block of the anterior holder 433D is positioned near the middle bottom side of the intraoral dental imaging sensor 430 near the exit of the connection 432. Accordingly, the intraoral dental imaging sensor 430 or the image processing unit 440 may determine that the holder 433 is the anterior holder 433D based at least in part on data from an accelerometer and a magnetic field sensor. The accelerometer provides orientation data indicating the orientation of the intraoral dental imaging sensor 430. For example, the orientation data indicates the exit of the connection 432 out of the mouth of the patient 431 is at the bottom right corner. The magnetic field provides magnetic field data indicating the position of the magnet 434D. For example, the magnet 434D is at the middle bottom side near the exit of the connection 432.

In the example of FIG. 33, the intraoral dental imaging sensor 430 is positioned by the bite block of the anterior holder 433D at the upper anterior middle position within the mouth of the patient 431. Compared to the intraoral dental imaging sensor 430 of FIG. 32, the intraoral dental imaging sensor 430 of FIG. 33 is oriented in the same manner, but positioned in the middle of the mouth of the patient 431. That is, the connection 432 exits at the bottom right out of the mouth of the patient 431 as shown by the arrow indicating the orientation of the intraoral dental imaging sensor 430. Accordingly, the intraoral dental imaging sensor 430 can capture image data of the upper anterior middle position of the mouth of the patient 431 and transmit the image data to an image processing unit 440 over connection 432. As illustrated in FIG. 33, the magnet 434D attached to the bite block of the anterior holder 433D is positioned near the middle bottom side of the intraoral dental imaging sensor 430 near the exit of the connection 432. Accordingly, the intraoral dental imaging sensor 430 or the image processing unit 440 may determine that the holder 433 is the anterior holder 433D based at least in part on data from an accelerometer and a magnetic field sensor. The accelerometer provides orientation data indicating the orientation of the intraoral dental imaging sensor 430. For example, the orientation data indicates the exit of the connection 432 out of the mouth of the patient 431 is at the bottom right corner. The magnetic field provides magnetic field data indicating the position of the magnet 434D. For example, the magnet 434D is at the middle bottom side near the exit of the connection 432.

In the example of FIG. 34, the intraoral dental imaging sensor 430 is positioned by the bite block of the anterior holder 433D at the upper anterior right position within the mouth of the patient 431. Compared to the intraoral dental imaging sensor 430 of FIG. 32, the intraoral dental imaging sensor 430 of FIG. 34 is oriented in same manner, but positioned towards the right of the mouth of the patient 431. That is, the connection 432 exits at the bottom right of the mouth of the patient 431 as shown by the arrow indicating the orientation of the intraoral dental imaging sensor 430. Accordingly, the intraoral dental imaging sensor 430 can capture image data of the upper anterior right position of the mouth of the patient 431 and transmit the image data to an image processing unit 440 over connection 432. As illustrated in FIG. 34, the magnet 434D attached to the bite block of the anterior holder 433D is positioned near the middle bottom side of the intraoral dental imaging sensor 430 near the exit of the connection 432. Accordingly, the intraoral dental imaging sensor 430 or the image processing unit 440 may determine that the holder 433 is the anterior holder 433D based at least in part on data from an accelerometer and a magnetic field sensor. The accelerometer provides orientation data indicating the orientation of the intraoral dental imaging sensor 430. For example, the orientation data indicates the exit of the connection 432 out of the mouth of the patient 431 is at the bottom right corner. The magnetic field provides magnetic field data indicating the position of the magnet 434D. For example, the magnet 434D is at the middle bottom side near the exit of the connection 432.

Figures 35, 36, 37:
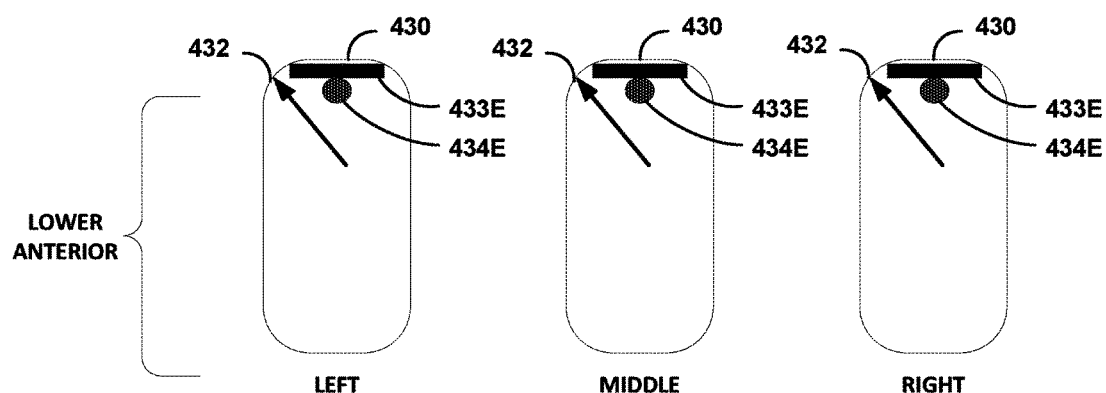
FIGS. 35-37 are schematic views of an intraoral dental imaging sensor and a bite block of a lower anterior holder with a magnet.

FIGS. 35-37 are schematic views of an intraoral dental imaging sensor 430 and a bite block of an anterior holder 433E with a magnet 434E. FIGS. 35-37 are described with from the perspective of the intraoral dental imaging sensor 430 and the image processing unit 440 as described above. In some embodiments, the anterior holder 433E is similar to the anterior holder 433D as described above.

In the example of FIG. 35, the intraoral dental imaging sensor 430 is positioned by the bite block of the anterior holder 433E at the lower anterior left position within the mouth of the patient 431. In this example, the connection 432 exits at the top left out of the mouth of the patient 431 as shown by the arrow indicating the orientation of the intraoral dental imaging sensor 430. Accordingly, the intraoral dental imaging sensor 430 can capture image data of the lower anterior left position of the mouth of the patient 431 and transmit the image data to an image processing unit 440 over connection 432. As illustrated in FIG. 35, the magnet 434E attached to the bite block of the anterior holder 433E is positioned near the middle top side of the intraoral dental imaging sensor 430 near the exit of the connection 432. Accordingly, the intraoral dental imaging sensor 430 or the image processing unit 440 may determine that the holder 433 is the anterior holder 433E based at least in part on data from an accelerometer and a magnetic field sensor. The accelerometer provides orientation data indicating the orientation of the intraoral dental imaging sensor 430. For example, the orientation data indicates the exit of the connection 432 out of the mouth of the patient 431 is at the top left corner. The magnetic field provides magnetic field data indicating the position of the magnet 434E. For example, the magnet 434E is at the middle top side near the exit of the connection 432.

In the example of FIG. 36, the intraoral dental imaging sensor 430 is positioned by the bite block of the anterior holder 433E at the lower anterior middle position within the mouth of the patient 431. Compared to the intraoral dental imaging sensor 430 of FIG. 35, the intraoral dental imaging sensor 430 of FIG. 36 is oriented in the same manner, but positioned in the middle of the mouth of the patient 431. That is, the connection 432 exits at the top left out of the mouth of the patient 431 as shown by the arrow indicating the orientation of the intraoral dental imaging sensor 430. Accordingly, the intraoral dental imaging sensor 430 can capture image data of the lower anterior middle position of the mouth of the patient 431 and transmit the image data to an image processing unit 440 over connection 432. As illustrated in FIG. 36, the magnet 434E attached to the bite block of the anterior holder 433E is positioned near the middle top side of the intraoral dental imaging sensor 430 near the exit of the connection 432. Accordingly, the intraoral dental imaging sensor 430 or the image processing unit 440 may determine that the holder 433 is the anterior holder 433E based at least in part on data from an accelerometer and a magnetic field sensor. The accelerometer provides orientation data indicating the orientation of the intraoral dental imaging sensor 430. For example, the orientation data indicates the exit of the connection 432 out of the mouth of the patient 431 is at the top left corner. The magnetic field provides magnetic field data indicating the position of the magnet 434E. For example, the magnet 434E is at the middle top side near the exit of the connection 432.

In the example of FIG. 37, the intraoral dental imaging sensor 430 is positioned by the bite block of the anterior holder 433E at the lower anterior right position within the mouth of the patient 431. Compared to the intraoral dental imaging sensor 430 of FIG. 35, the intraoral dental imaging sensor 430 of FIG. 37 is oriented in same manner, but positioned towards the right of the mouth of the patient 431. That is, the connection 432 exits at the top left of the mouth of the patient 431 as shown by the arrow indicating the orientation of the intraoral dental imaging sensor 430. Accordingly, the intraoral dental imaging sensor 430 can capture image data of the lower anterior right position of the mouth of the patient 431 and transmit the image data to an image processing unit 440 over connection 432. As illustrated in FIG. 37, the magnet 434E attached to the bite block of the anterior holder 433E is positioned near the middle top side of the intraoral dental imaging sensor 430 near the exit of the connection 432. Accordingly, the intraoral dental imaging sensor 430 or the image processing unit 440 may determine that the holder 433 is the anterior holder 433E based at least in part on data from an accelerometer and a magnetic field sensor. The accelerometer provides orientation data indicating the orientation of the intraoral dental imaging sensor 430. For example, the orientation data indicates the exit of the connection 432 out of the mouth of the patient 431 is at the top left corner. The magnetic field provides magnetic field data indicating the position of the magnet 434E. For example, the magnet 434E is at the middle top side near the exit of the connection 432.

Although FIGS. 20-37 have been described as differentiating between various positions and holders. It is understood that orientation data from the accelerometer within the intraoral dental imaging sensor 430 can differentiate between left and right posterior/bitewing positions and holders. It is also understood that orientation data from the accelerometer within the intraoral dental imaging sensor 430 can differentiate between upper and lower anterior positions and holders. Further, in combination with the orientation data, it is understood that magnetic field data from the magnetic field sensor within the intraoral dental imaging sensor 430 can differentiate between upper posterior/bitewing/lower posterior positions and holders using the magnetic field data associated with the magnet attached to the holder. Finally, in combination with the orientation data and the magnetic field data described above, it is understood that magnetic field data from the magnetic field sensor within the intraoral dental imaging sensor 430 can differentiate between back/front and left/right/middle positions using the magnetic field data associated with the reference magnet, as described below with regard to FIGS. 38A and 38B. In other words, a reference magnet in combination with the magnet attached to the holder and the accelerometer are required in order to differentiate the respective back/front and left/right/middle positions of the posterior/bitewing/anterior positions and holders. In this way, the intraoral dental imaging sensor 430 and/or the image processing unit 440 may differentiate each image in a full mouth series of images using the orientation data and the magnetic field data.

It is understood that in FIGS. 20-31, the intraoral dental imaging sensor 430 may be inserted into the holder 433 as described above in two different directions thereby changing the relative position of the magnetic sensor and the holder magnet. In this way, the intraoral dental imaging sensor 430 is in a first position (i.e., a first position in the mouth of the patient 431) for FIGS. 20, 21, 30, and 31, and a second position for FIGS. 22, 23, 28, and 29. Similarly for the bitewing type of the holder 433, the intraoral dental imaging sensor 430 is in the a third position for FIGS. 24 and 25 and is in a fourth position for FIGS. 26 and 27. It is also understood that the intraoral dental imaging sensor 430 is in fifth position for FIGS. 32-34, and a sixth position for FIGS. 35-37.

Figure 38A:
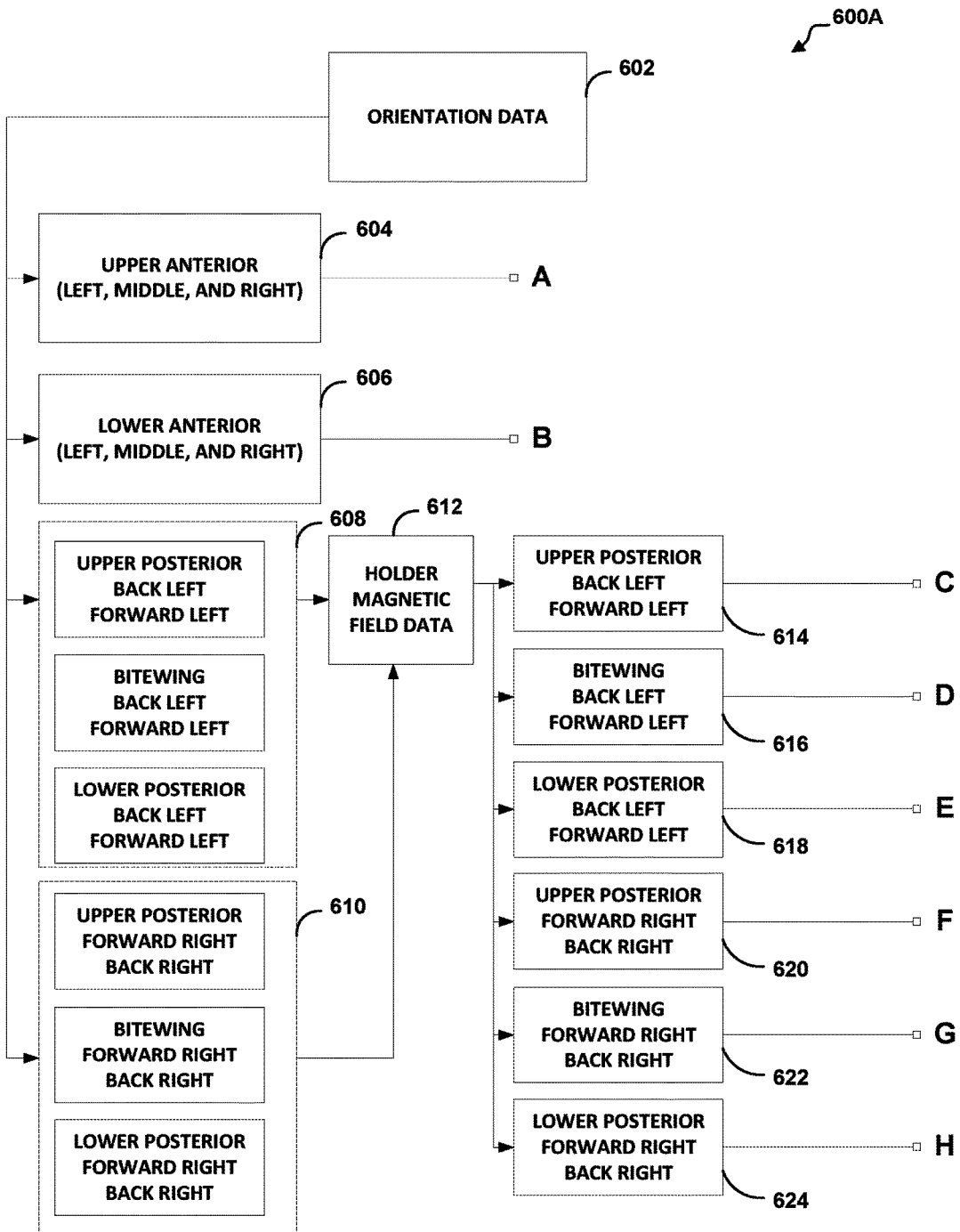

FIGS. 38A and 38B are flowcharts of a method 600 for capturing and organizing a full mouth series of images in a particular sequence from the intraoral dental imaging sensor 512 using the dental x-ray system 510 of FIG. 19. FIGS. 38A and 38B are described from the perspective of the intraoral dental imaging sensors 512 and the image processing unit 540 as described above.

In the example of FIG. 38A, the image processing unit 540 may receive image data captured by an intraoral dental imaging sensor 512 corresponding to a full mouth series of images along with metadata associated with each image. For example, the image processing unit 540 may receive orientation data 602 which is associated with image data and which indicates the orientation of the sensor 430 with respect to the earth's gravitational field. The image processing unit 540 can use the orientation data 602 to determine whether each image in the image data is in the left side or the right side of the mouth of the patient 431. In other words, the orientation data 602 can indicate the difference in the position of the intraoral dental imaging sensor 430, for example, the left side of the mouth of the patient 431 (as illustrated in FIGS. 20, 21, 24, 25, 28, and 29) or the right side of the mouth (as illustrated in FIGS. 22, 23, 26, 25, 30, and 31) as described above. The orientation data 602 can also distinguish the anterior position of the intraoral dental imaging sensor 430 between FIGS. 32-37.

For example, the image processing unit 540 can use the orientation data 602 to determine whether each image in the image data is in a group defined as upper anterior 604 (e.g., left, middle, or right, as illustrated in FIGS. 32-34) or in a group defined as lower anterior 606 (e.g., left, middle, or right, as illustrated in FIGS. 35-37). The image processing unit 540 can also use the orientation data 602 to determine whether each image in the image data is part of a group of positions 608 defined as upper posterior back left, upper posterior forward left, bitewing back left, bitewing forward left, lower posterior back left, or lower posterior forward left. The image processing unit 540 can also use the orientation data 602 to determine whether the image data is part of a group of positions 610 defined as upper posterior back right, upper posterior forward right, bitewing back right, bitewing forward right, lower posterior back right, or lower posterior forward right. It is understood that the image processing unit 540 can use the orientation data 602 to differentiate between the groups 604-610 as illustrated in FIG. 38A.

In the example of FIG. 38A, as part of the metadata associated with each image in the image data, the image processing unit 540 also receives holder magnetic field data 612 associated with a magnet attached to a holder (e.g., the magnet 434 as described above). The image processing unit 540 can use the holder magnetic field data 612 to determine a type of the holder 433 as described above. In this way, the image processing unit 540 can determine whether the image is part of a subgroup in the group of positions 608. For example, the image processing unit 540 can determine with the holder magnetic field data 612 whether the image is part of one of the subgroups defined as upper posterior back left/upper posterior forward left 614, bitewing back left/bitewing forward left 616, lower posterior back left/lower posterior forward left 618, upper posterior back right/upper posterior forward right 620, bitewing back right/bitewing forward right 622, or lower posterior back right/lower posterior forward right 624. Based on the above determinations, the image processing unit 540 can also differentiate between the different groups. For example, in the illustrated embodiment, the images in the upper anterior group 604 are defined as group A. The images in the lower anterior group 606 are defined as group B. The images in the upper posterior back left/upper posterior forward left subgroup 614 are defined as group C. The images in the bitewing back left/bitewing forward left subgroup 616 are defined as group D. The images in the lower posterior back left/lower posterior forward left subgroup 618 are defined as group E. The images in the upper posterior back right/upper posterior forward right subgroup 620 are defined as group F. The images in the bitewing back right/bitewing forward right subgroup 622 are defined as group G. The images in the lower posterior back right/lower posterior forward right subgroup 624 are defined as group H. Accordingly, the image processing unit 540 can assign each image in the full mouth series of images to groups A-H.

In the example of FIG. 38B, as part of the metadata associated with each image in the image data, the image processing unit 540 also receives an external magnetic field data 626 associated with a reference magnet mounted on a holder or a patient (e.g., the reference magnet 435 as described with regard to FIG. 18). The image processing unit 540 can use the external magnetic field data 626 to determine the organization of the image data of groups A-H. For example, the image processing unit 540 can determine with the external magnetic field data 626 whether each image of the image data corresponds to a particular image of a full mouth series of images 628. For example, the image processing unit 540 can process the images in groups A-H with the external magnetic field data 626, and determine whether each image is defined as upper posterior back left 628A, upper posterior forward left 628B, bitewing back left 628C, bitewing forward left 628D, lower posterior back left 628E, lower posterior forward left 628F, upper posterior front right 628G, upper posterior back right 628H, bitewing front right 628J, bitewing back right 628K, lower posterior front right 628L, lower posterior back right 628M, upper anterior left 628N, upper anterior middle, 628O, upper anterior right 628P, lower anterior left 628Q, lower anterior middle 628R, or lower anterior right 628S. Accordingly, the image processing unit 540 can determine the exact position of each image in the image data captured by the intraoral dental imaging sensor 512 regardless of the order the images. After processing the images in groups A-H, in some embodiments, the image processing unit 540 may output the full mouth series of images 628 to a display as an image (e.g., image 444 as illustrated in FIG. 18). Thus, the combination of all three kinds of data—the orientation data 602, the holder magnetic field data 612, and the external magnetic field data 626 (from the magnet mounted on the patient)—allows the image processing unit 540 to determine unambiguously which shot of the x-ray series is being taken.

Figure 39:
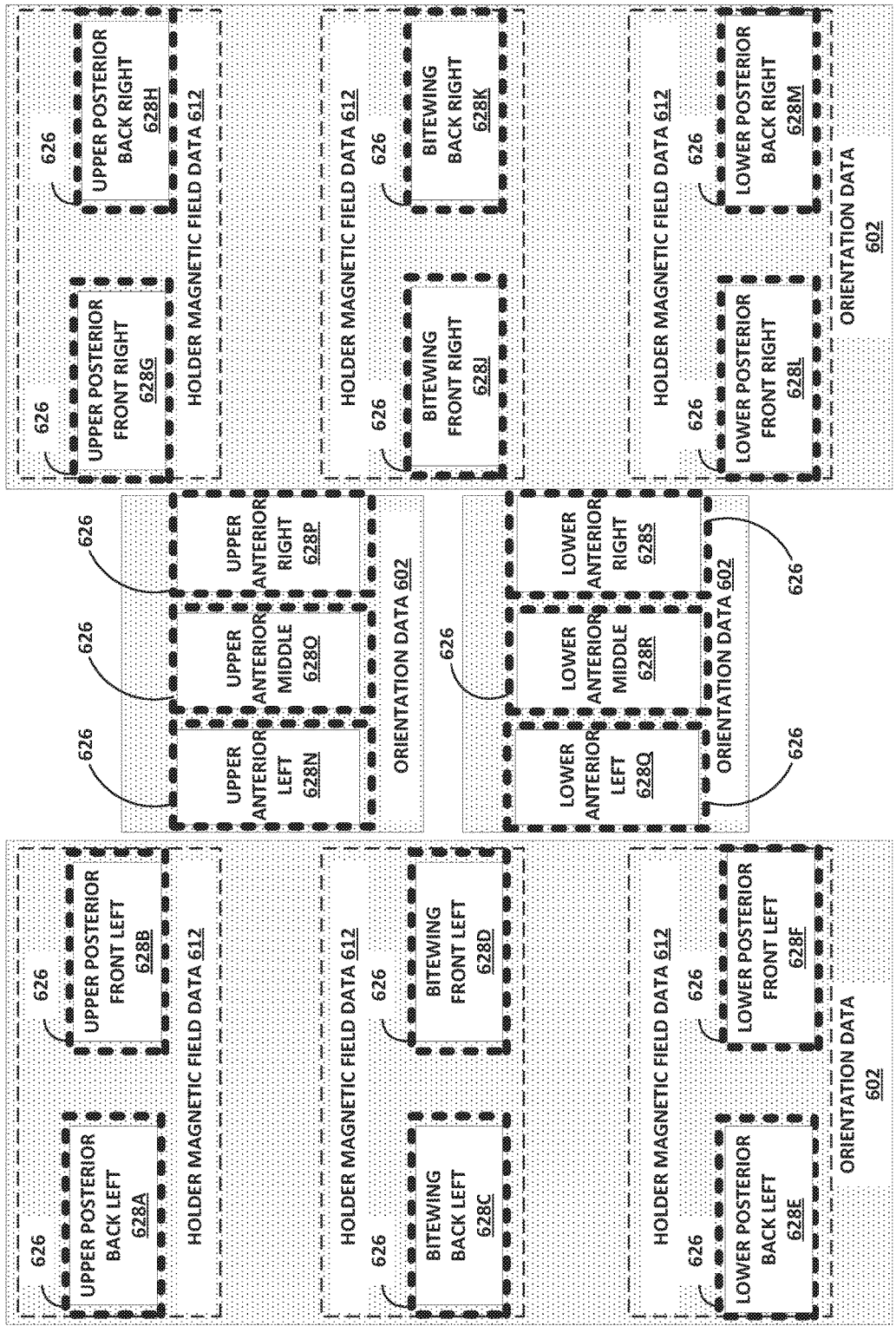
FIG. 39 is a block diagram of the groups of images that an image processing unit can define using the orientation data, the holder magnetic field data, or the external magnetic field data of FIGS. 38A and 38B.

FIG. 39 is a block diagram of the groups of images that an image processing unit can define using the orientation data 602, the holder magnetic field data 612, or the external magnetic field data 626 of FIGS. 38A and 38B. FIG. 39 illustrates a simplified view of the processing performed in FIGS. 38A and 38B as described above.

As illustrated in FIG. 39, the image processing unit 540 can use the orientation data 602 (grouped by the grey boxes) to differentiate between four groups. One group includes images from the upper posterior back left 628A, the upper posterior forward left 628B, the bitewing back left 628C, the bitewing forward left 628D, the lower posterior back left 628E, and the lower posterior forward left 628F. Another group includes images from the posterior front right 628G, the upper posterior back right 628H, the bitewing front right 628J, the bitewing back right 628K, the lower posterior front right 628L, and the lower posterior back right 628M. Another group includes images from the upper anterior left 628N, the upper anterior middle, 628O, and the upper anterior right 628P. Yet another group includes images from the lower anterior left 628Q, the lower anterior middle 628R, and the lower anterior right 628S.

Additionally or alternatively to the orientation data 602 as described above, the image processing unit 540 can use the holder magnetic field data 612 (grouped by the light dotted lines) to differentiate between six groups of images. One group includes images from the upper posterior back left 628A and the upper posterior forward left 628B. Another group includes images from the bitewing back left 628C and the bitewing forward left 628D. Another group includes images from the lower posterior back left 628E and the lower posterior forward left 628F. Another group includes images from the posterior front right 628G and the upper posterior back right 628H. Another group includes images from the bitewing front right 628J and the bitewing back right 628K, Yet another group includes images from the lower posterior front right 628L, and the lower posterior back right 628M.

Additionally or alternatively to the orientation data 602 and/or the holder magnetic field data 612 as described above, the image processing unit can use the external magnetic field data 626 (grouped by the large dotted lines) to differentiate between each of the eighteen images. In this way, the image processing unit can determine whether each image is defined as upper posterior back left 628A, upper posterior forward left 628B, bitewing back left 628C, bitewing forward left 628D, lower posterior back left 628E, lower posterior forward left 628F, upper posterior front right 628G, upper posterior back right 628H, bitewing front right 628J, bitewing back right 628K, lower posterior front right 628L, lower posterior back right 628M, upper anterior left 628N, upper anterior middle, 628O, upper anterior right 628P, lower anterior left 628Q, lower anterior middle 628R, or lower anterior right 628S. Accordingly, the image processing unit 540 can determine the exact position of each image in the image data captured by the intraoral dental imaging sensor 512 regardless of the order the images are acquired.

Figure 40:
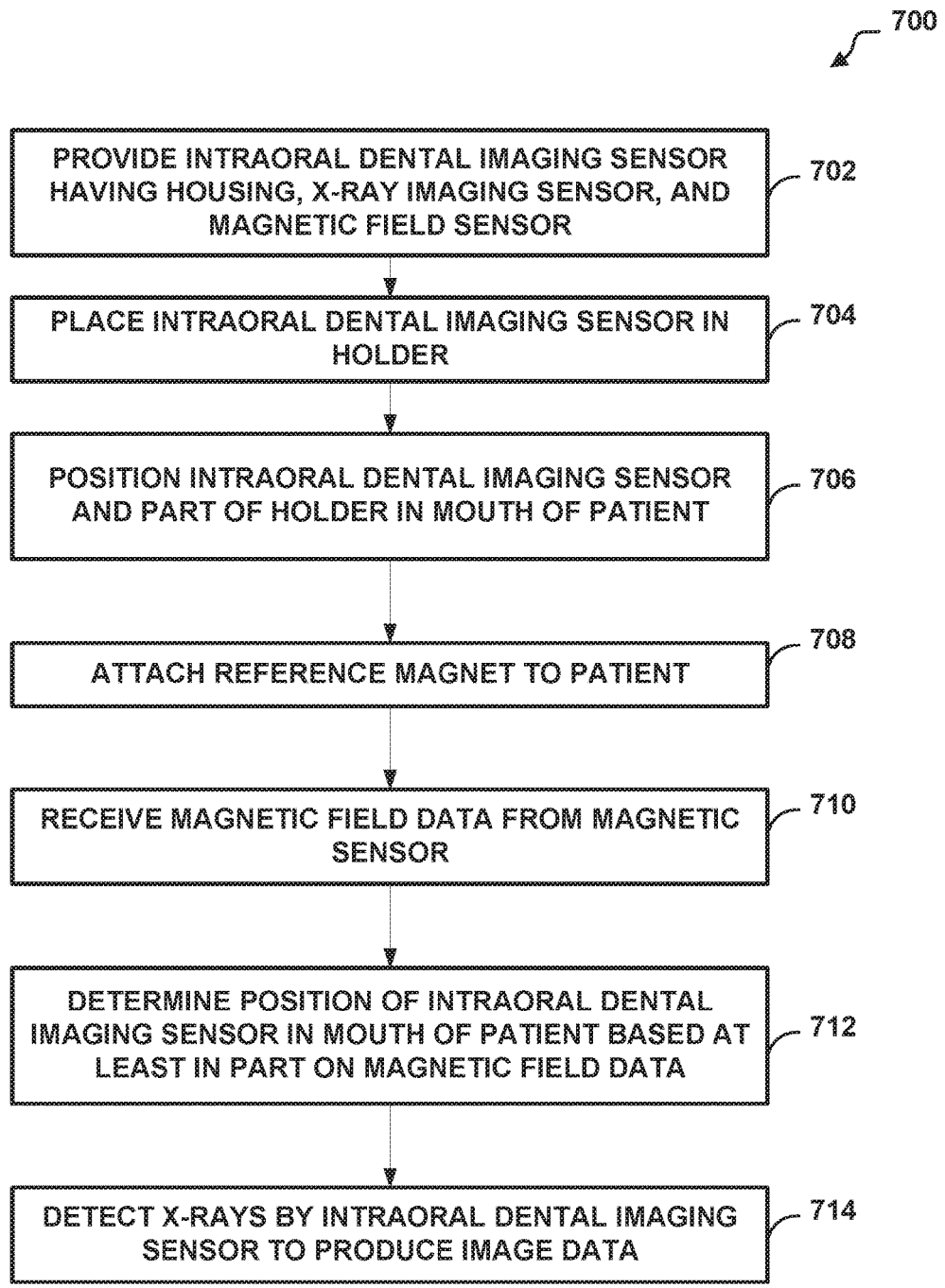
FIG. 40 is a flowchart of a method for intraoral dental imaging using the intraoral dental imaging sensor of the dental x-ray system of FIG. 18.

FIG. 40 is a flowchart of a method 700 for intraoral dental imaging using the intraoral dental imaging sensor 430 of the dental x-ray system 410 of FIG. 18. In the example of FIG. 40, at block 702, a user (e.g., the patient 431, a technician, or other suitable person) provides an intraoral dental imaging sensor 430 having a housing, an x-ray imaging sensor located in the housing, and a magnetic field sensor disposed in or on the housing. At block 704, the user (e.g., the patient 431, a technician, or other suitable person) places the intraoral dental imaging sensor in a holder. At block 706, the user (e.g., the patient 431, a technician, or other suitable person) positions the intraoral dental imaging sensor 430 and at least part of the holder in a mouth of a patient 431. In some embodiments, the positioning of the intraoral dental imaging sensor 430 may be at an unknown position in the mouth of the patient 431. At block 708, the user (e.g., the patient 431, a technician, or other suitable person or device) attaches a reference magnet 435 to the patient 431. At block 710, a processing unit 440A (e.g., an electronic processor) receives magnetic field data from the magnetic field sensor disposed in or on the housing of the intraoral dental imaging sensor 430. At block 712, the processing unit 440A determines a position of the intraoral dental imaging sensor 430 in the mouth of the patient 431 based at least in part on the magnetic field data from the magnetic field sensor. At block 714, the x-ray imaging sensor located in the housing of the intraoral dental imaging sensor 430 detects x-rays and produces image data.

In some embodiments, the method 700 further includes an accelerometer disposed in or on the housing and configured to detect an orientation of the housing and output orientation data based on the orientation of the housing, and the processing unit 440A receives orientation data from an accelerometer and determines an orientation of the intraoral dental imaging sensor 430 relative to gravity based at least in part on the orientation data. In some embodiments, the method 700 further includes the processing unit 440A determining a relative position in the mouth of the patient 431 based at least in part on the orientation data and the magnetic field data. In some embodiments, the method 700 further includes the processing unit 440A determining a type of the holder based at least in part on the magnetic field data.

In some embodiments, the method 700 further includes the processing unit 440A receiving image data from the x-ray sensor located in the housing of the intraoral dental imaging sensor 430, generating images from the image data, and organizing the images (e.g., a full mouth series of images 628 as illustrated in FIG. 38B, a subset of a full mouth series, or images outside of the full mouth series) in a sequence based at least in part on the one or more characteristics of the intraoral dental imaging sensor 430. In some embodiments, the method 700 further includes the processing unit 440A displaying the images (e.g., the full mouth series of images, a subset thereof, or images outside of the full mouth series) organized in the sequence on a display device 443.

It should be understood that the intraoral dental imaging sensor 430 of FIG. 18 could be configured to carry out all or a portion of the image processing carried out by the processing unit 440A of the image processing unit 440. That is, the intraoral dental imaging sensor 430 may include one or more electronic processors as illustrated in FIG. 19. In other words, imaging processing may be distributed between the intraoral dental imaging sensor 430 and the image processing unit 440. For example, processing hardware may be located in the body of the intraoral dental imaging sensor 430 or in the connection 432 connecting the intraoral dental imaging sensor 430 to the image processing unit 440.

Thus, the invention provides, among other things, systems, apparatuses, and methods for capturing and organizing images acquired with a dental x-ray system. In some embodiments, the systems, apparatuses, and methods can determine a type of holder and whether an image corresponds to a particular image in a full mouth series of images using orientation data, magnetic field data, or both. It should be understood that the systems, apparatuses, and methods disclosed herein can be used in other types of imaging systems and is not limited to dental x-ray imaging. Furthermore, it should be understood that the functionality performed by the intraoral dental imaging sensor 512 and the image processing unit 540 can be combined and distributed in numerous configurations. Various features and advantages of the invention are set forth in the following claims.

What is claimed is:

1. A dental x-ray system comprising:
   an intraoral dental imaging sensor having
      a housing,
      an x-ray imaging sensor located in the housing and configured to capture x-ray energy and output x-ray image data, and
      a magnetic field sensor disposed in or on the housing and configured to sense one or more magnetic fields and output magnetic field data based on the one or more magnetic fields;
   a holder configured to position the intraoral dental imaging sensor in a mouth of a patient;
   a reference magnet configured to be disposed on the patient; and
   an image processing unit communicatively coupled to the intraoral dental imaging sensor and having
      memory, and
      an electronic processor electrically coupled to the memory and configured to receive the magnetic field data from the magnetic field sensor, and
         determine a position of the intraoral dental imaging sensor in the mouth of the patient based at least in part on the magnetic field data.

2. The system of claim 1, further comprising an accelerometer disposed in or on the housing and configured to detect an orientation of the housing and output orientation data based on the orientation of the housing, wherein the electronic processor is further configured to receive the orientation data from the accelerometer and determine an orientation of the intraoral dental imaging sensor relative to gravity based at least in part on the orientation data.

3. The system of claim 2, wherein the electronic processor is further configured to determine a relative position of the intraoral dental imaging sensor in the mouth of the patient based at least in part on the orientation data and the magnetic field data.

4. The system of claim 1, wherein the holder includes a magnet, and wherein the electronic processor is further configured to determine a type of the holder based at least in part on the magnetic field data.

5. The system of claim 1, wherein the electronic processor is further configured to
   receive image data from the x-ray imaging sensor,
   generate images from the image data, and
   organize the images in a sequence based at least in part on the magnetic field data.

6. The system of claim 5, further comprising a display, wherein the electronic processor is further configured to output the images to the display organized in the sequence based at least in part on the magnetic field data.

7. An intraoral dental imaging sensor comprising:
   a housing;
   an x-ray imaging sensor located in the housing and configured to receive x-rays and output image data;
   a magnetic field sensor disposed in or on the housing and configured to sense one or more magnetic fields and output magnetic field data; and
   an electronic processor configured to
      receive the magnetic field data, and
      determine a position of the intraoral dental imaging sensor in a mouth of a patient based at least in part on the magnetic field data.

8. The intraoral dental imaging sensor of claim 7, further comprising an accelerometer disposed in or on the housing and configured to detect an orientation of the housing and output orientation data, wherein the electronic processor is further configured to receive the orientation data and determine an orientation of the intraoral dental imaging sensor relative to gravity based at least in part on the orientation data.

9. The intraoral dental imaging sensor of claim 8, wherein the electronic processor is further configured to determine a relative position of the intraoral dental imaging sensor in a mouth of a patient based at least in part on the orientation data and the magnetic field data.

10. The intraoral dental imaging sensor of claim 7, wherein the electronic processor is further configured to determine a type of a holder based at least in part on the magnetic field data.

11. A method for intraoral dental imaging, the method comprising:
    providing an intraoral dental imaging sensor having a housing, an x-ray imaging sensor located in the housing, and a magnetic field sensor disposed in or on the housing;
    placing the intraoral dental imaging sensor in a holder;
    positioning the intraoral dental imaging sensor and at least part of the holder in a mouth of a patient;
    attaching a reference magnet to the patient;
    receiving, by an electronic processor, magnetic field data from the magnetic field sensor;
    determining, by the electronic processor, a position of the intraoral dental imaging sensor in the mouth of the patient based at least in part on the magnetic field data; and
    detecting x-rays by the intraoral dental imaging sensor to produce image data.

12. The method of claim 11, further comprising
    receiving, by the electronic processor, orientation data from an accelerometer disposed in or on the housing of the intraoral dental imaging sensor; and
    determining, by the electronic processor, an orientation of the intraoral dental imaging sensor relative to gravity based at least in part on the orientation data.

13. The method of claim 12, further comprising determining, by the electronic processor, a relative position in the mouth of the patient based at least in part on the orientation data and the magnetic field data.

14. The method of claim 11, further comprising determining, by the electronic processor, a type of the holder based at least in part on the magnetic field data.

15. The method of claim 11, further comprising:
receiving, by the electronic processor, the image data from an x-ray imaging sensor located in the housing of the intraoral dental imaging sensor;
generating, by the electronic processor, images from the image data; and
organizing, by the electronic processor, the images in a sequence based at in part on the position of the intraoral dental imaging sensor in the mouth of the patient.

16. The method of claim 15, further comprising displaying, by the electronic processor, the images organized in the sequence on a display.

17. A non-transitory computer-readable medium comprising instructions that when executed by an electronic processor perform a set of functions comprising:
receiving magnetic field data from a magnetic field sensor disposed in or on a housing of an intraoral dental imaging sensor; and
determining a position of the intraoral dental imaging sensor in a mouth of a patient based at least in part on the magnetic field data.

18. The non-transitory computer-readable medium of claim 17, further comprising instructions that when executed by the electronic processor perform a set of functions comprising:
receiving orientation data from an accelerometer disposed in or on the housing; and
determining an orientation of the intraoral dental imaging sensor relative to gravity based at least in part on the orientation data.

19. The non-transitory computer-readable medium of claim 18, further comprising instructions that when executed by the electronic processor perform a function comprising determining a relative position in a mouth of a patient based at least in part on the orientation data and the magnetic field data.

20. The non-transitory computer-readable medium of claim 17, further comprising instructions that when executed by the electronic processor perform a function comprising determining a type of a holder based at least in part on the magnetic field data.

21. The non-transitory computer-readable medium of claim 17, further comprising instructions that when executed by the electronic processor perform a set of functions comprising
receiving image data from an x-ray imaging sensor located in the housing;
generating images from the image data; and
organizing the images in a sequence based at least in part on the position of the intraoral dental imaging sensor in the mouth of the patient.

22. The non-transitory computer-readable medium of claim 21, further comprising instructions that when executed by the electronic processor perform a function comprising displaying the images organized in the sequence on a display.

23. A holder for an intraoral dental imaging sensor, the holder comprising:
a housing configured to position and support a housing of the intraoral dental imaging sensor in a mouth of a patient; and
a magnet attached to the housing of the holder, wherein a characteristic of the magnet is configured to indicate a type of the holder.

24. The holder of claim 23, wherein the housing of the holder is configured to position and support the intraoral dental imaging sensor at one of a plurality of anterior positions, a plurality of posterior positions, or a plurality of bitewing positions in the mouth of the patient, and
wherein the type of the holder is based on the housing of the holder that is configured to position and support the intraoral dental imaging sensor at the one of the plurality of anterior positions, the plurality of posterior positions, or the plurality of bitewing positions in the mouth of the patient.

* * * * *